(12) United States Patent
Liu et al.

(10) Patent No.: US 10,392,436 B2
(45) Date of Patent: Aug. 27, 2019

(54) ANTI-HUMAN IL-17 MONOCLONAL ANTIBODIES AND USE THEREOF

(71) Applicants: BEIJING BETTERMAB BIOTECHNOLOGY CO., LTD, Beijing (CN); BEIJING WISDOMAB BIOTECHNOLOGY CO., LTD, Beijing (CN); GENRIX (SHANGHAI) BIOPHARMACEUTICAL CO. LTD., Shanghai (CN); CHONGQING GENRIX BIOPHARMACEUTICAL CO., LTD., Chongqing (CN)

(72) Inventors: Zhigang Liu, Beijing (CN); Shijie Shen, Beijing (CN); Yulan Liu, Beijing (CN); Jingjing Guo, Beijing (CN); Xiaobo Hao, Beijing (CN)

(73) Assignees: BEIJING BETTERMAB BIOTECHNOLOGY CO., LTD (CN); BEIJING WISDOMAB BIOTECHNOLOGY CO., LTD (CN); GENRIX (SHANGHAI) BIOPHARMACEUTICAL CO. LTD. (CN); CHONGQING GENRIX BIOPHARMACEUTICAL CO., LTD. (CN)

( * ) Notice: Subject to any disclaimer, the term of this patent is extended or adjusted under 35 U.S.C. 154(b) by 0 days.

(21) Appl. No.: 15/510,655

(22) PCT Filed: Feb. 29, 2016

(86) PCT No.: PCT/CN2016/074805
§ 371 (c)(1),
(2) Date: Mar. 10, 2017

(87) PCT Pub. No.: WO2016/138842
PCT Pub. Date: Sep. 9, 2016

(65) Prior Publication Data
US 2017/0327571 A1    Nov. 16, 2017

(30) Foreign Application Priority Data

Mar. 5, 2015  (CN) .......................... 2015 1 0097117

(51) Int. Cl.
*C07K 16/24* (2006.01)
*A61K 39/395* (2006.01)
*A61K 39/00* (2006.01)

(52) U.S. Cl.
CPC .......... *C07K 16/244* (2013.01); *A61K 39/395* (2013.01); *C07K 16/24* (2013.01); *A61K 2039/505* (2013.01); *C07K 2317/21* (2013.01); *C07K 2317/52* (2013.01); *C07K 2317/54* (2013.01); *C07K 2317/55* (2013.01); *C07K 2317/565* (2013.01); *C07K 2317/56* (2013.01); *C07K 2317/622* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| 7,807,155 | B2 | 10/2010 | Di Padova et al. |
| 8,753,843 | B2 | 6/2014 | Presta et al. |
| 2010/0080812 | A1 | 4/2010 | Auer et al. |
| 2011/0236390 | A1 | 9/2011 | Almagro et al. |
| 2013/0202591 | A1 | 8/2013 | Horlick et al. |
| 2017/0327571 | A1 | 11/2017 | Liu et al. |

FOREIGN PATENT DOCUMENTS

| CN | 102164959 A | 8/2011 |
| CN | 102905727 A | 1/2013 |
| CN | 103154026 A | 6/2013 |
| CN | 103936854 A | 7/2014 |
| CN | 105315371 A | 2/2016 |
| RU | 2402569 C2 | 10/2010 |
| WO | 2005/090407 A1 | 9/2005 |
| WO | 2007/117749 A2 | 10/2007 |
| WO | 2007/149032 A1 | 12/2007 |
| WO | 2008/001063 A1 | 1/2008 |
| WO | 2008/047134 A2 | 4/2008 |
| WO | 2010/034443 A1 | 4/2010 |
| WO | 2011/053763 A2 | 5/2011 |
| WO | 2015/022656 A1 | 2/2015 |
| WO | 2016/138842 A1 | 9/2016 |

OTHER PUBLICATIONS

Lubberts et al, EMJ Rheumatology. 2015, vol. 2, No. 1, pp. 55-64.*
Van Den Berg et al, (Seminars in Arthritis and Rheumatism, 2013, vol. 43, pp. 158-170.*
Wells, 1990, Biochemistry 29:8509-8517.*
Bork, 2000, Genome Research 10:398-400.*
Skolnick et al., 2000, Trends in Biotech. 18(1):34-39.*
Doerks et al., 1998, Trends in Genetics 14:248-250.*
Tokuriki and Tawflik, Current Opinion in Structural Biology 2009, 19: 596-604.*
Brummell et al, Biochemistry; 1993; vol. 32, pp. 1180-1187.*
Kobayashi et al. Protein Engineering; 1999; vol. 12, pp. 879-844.*
Brorson et al. J. Immunol; 1999; vol. 163, pp. 6694-6701.*

(Continued)

*Primary Examiner* — Bridget E Bunner
*Assistant Examiner* — Fozia Hamud
(74) *Attorney, Agent, or Firm* — Lathrop Gage LLP; James H. Velema, Esq.

(57) ABSTRACT

The present application discloses a novel anti-human IL-17 monoclonal antibody obtained by phage antibody library screening and genetic engineering, or a functional fragment thereof, a polynucleotide encoding the monoclonal antibody or the functional fragment thereof, a vector comprising the polynucleotide, a host cell comprising the polynucleotide or vector, a method for preparing and purifying the antibody, and use of the antibody or the functional fragment thereof.

17 Claims, 5 Drawing Sheets
Specification includes a Sequence Listing.

(56) References Cited

OTHER PUBLICATIONS

Coleman Research in Immunol; 1994; vol. 145; pp. 33-36.*
Jang et al. (Molec. Immunol; 1998, vol. 35, pp. 1207-1217.*
Gaffen (2009) "Structure and signalling in the IL-17 receptor family," Nat. Rev. Immunol. 9(8):556-567.
Hwang et al. (2004) "IL-17 induces production of IL-6 and IL-8 in rheumatoid arthritis synovial fibroblasts via NF-κB-and PI3-kinase/Akt-dependent pathways," Arthritis Research & Therapy. 6(2):R120-R128.
Witkowski et al. (2004) "Interleukin-17: a mediator of inflammatory responses," Cell. Mol. Life Sci. 61:567-579.
International Search Report corresponding to International Patent Application No. PCT/CN2016/074805, dated May 24, 2016.
Grantham et al. (1974) "Amino acid difference formula to help explain protein evolution," Science. 185:862-864.
Brown et al. (Feb. 20, 2014) "Anti-IL-17 phase II data for psoriasis: A review," J. Dermatolog. Treat. 26(1):32-6.
Farahnik et al. (Mar. 2016) "Anti-IL-17 agents for psoriasis: A review for phase III dada," Journal of Drugs in Dermatology. 15(3):311-6.
Jeon et al. (Oct. 3, 2017) "Monoclonal antibodies inhibiting IL-12, 23 and -17 for the treatment of psoriasis," Hum. Vaccin. Inmmunother. 13(10):2247-2259.
Search Report corresponding to European Patent Application No. 16758458.0, dated Nov. 7, 2017.

* cited by examiner

SEQUENCE LISTING

```
<160> NUMBER OF SEQ ID NOS: 137

<210> SEQ ID NO 1
<211> LENGTH: 357
<212> TYPE: DNA
<213> ORGANISM: Homo sapiens
<220> FEATURE:
<223> OTHER INFORMATION: VH1

<400> SEQUENCE: 1
caggtgcagt tagtgcagag cggtgcggaa gtgaaaaaac cgggcagcag cgtgaaagtg      60
agctgcaaag cgagtggcgg caccttttagc agctatgcga ttagctgggt gcgtcaggca     120
ccgggacagg gcctggaatg gatgggccgt ataattccga ttctgggcat tgcgaactat     180
gcgcagaaat tccaaggccg cgtgaccatt accgcggaca aatctaccag caccgcgtat     240
atggaactga gcagcctgcg tagcgaggat accgctgtgt attattgcgc ccgtgcgcgt     300
gatttttgga gcggctgggg ctattggggc cagggcaccc tggtgactgt gtcatct       357

<210> SEQ ID NO 2
<211> LENGTH: 354
<212> TYPE: DNA
<213> ORGANISM: Homo sapiens
<220> FEATURE:
<223> OTHER INFORMATION: VH3

<400> SEQUENCE: 2
gaagtgcaat tggtggaaag cggtggcggt ctggtgcagc cgggtggcag cctgcgtctg      60
agctgcgcag cgagcggctt cacctttagc agctacgcga tgagctgggt gcgccaggca     120
ccgggtaaag gtctggaatg ggtgagcgcg attagcggta gcggcggcag cacctactat     180
gcggatagcg tgaaaggccg ttttaccatc tcgcgtgata actcgaaaaa caccctgtac     240
ctgcagatga acagcctgcg tgcggaagat accgcggtgt attattgcgc acgtgggtgg     300
agttataatg gggttgatcc ctggggtcag ggcactctgg tgaccgtgtc gagc           354

<210> SEQ ID NO 3
<211> LENGTH: 354
<212> TYPE: DNA
<213> ORGANISM: Homo sapiens
```

```
<220> FEATURE:
<223> OTHER INFORMATION: VH5

<400> SEQUENCE: 3
gaagttcaac tggttcaaag cggtgccgaa gtcaagaaac caggcgaaag cctcaaaatc      60
agctgcaaag gctctggtta taswttcacc avctactgga tcrgttgggt cgccagatg     120 ccaggcaaag gtctggaatg gatgggtaka attdacccar gtgacagcda caccavwtat    180
tctccaagct tccagggtca ggttactatc agcgcagaca aaagcatcag caccgcctat    240
ctgcagtgga gctctctcaa agccagcgat actgctatgt actattgtgc acgcgtttct    300
tcggtcgact acttcgatta ctggggtcaa ggtactctgg tcaccgtctc gagc          354

<210> SEQ ID NO 4
<211> LENGTH: 321
<212> TYPE: DNA
<213> ORGANISM: Homo sapiens
<220> FEATURE:
<223> OTHER INFORMATION: VK1

<400> SEQUENCE: 4
gatatccaga tgacccagag cccgagcagc ctgagcgcga gcgtgggtga tcgcgtgacc      60
attacctgcc gcgcgagcca gggcattagc agctatctgg cgtggtatca gcagaaaccg    120
ggtaaagcgc cgaaactgtt aatttatgcg gccagcagct tgcagagcgg cgtgccgtcg    180
cgttttagcg gctcgggttc gggcaccgat tttaccctga ccatctcgag cttgcagccg    240
gaggacttcg ccacctacta ttgccagaat gctgagctta ttttaacctt cggccagggc    300
accaaagtgg agatcaaacg c                                               321

<210> SEQ ID NO 5
<211> LENGTH: 330
<212> TYPE: DNA
<213> ORGANISM: Homo sapiens
<220> FEATURE:
<223> OTHER INFORMATION: VL3

<400> SEQUENCE: 5
gatatcgttc tgactcaatc tccggcaact ctgtctctgt ctccgggtga acgtgcaact     60
ctgtcttgtc gtgcatctca gtctgtgagc tctagttatc tggcatggta tcagcaaaaa    120
ccgggtcagg caccgcgtct gctgatttat ggtgcaagct ctcgtgcaac tggtgttccg    180
gcacgtttta gtggtagtgg tagcggcacc gatttactc tgactatctc gagtctggaa    240
ccggaggact tcgccgtgta ctattgccag cagttgatcg ataagctgta taccaccttc    300
ggccagggca ccaaagtgga gatcaaacgc                                      330

<210> SEQ ID NO 6
<211> LENGTH: 66
<212> TYPE: DNA
<213> ORGANISM: Pectobacterium carotovorum
<220> FEATURE:
<223> OTHER INFORMATION: pelB leader

<400> SEQUENCE: 6
atgaaatacc tattgcctac ggcagccgct ggattgttat tactcgctgc ccaaccagcc      60
atggcg                                                                66

<210> SEQ ID NO 7
<211> LENGTH: 696
<212> TYPE: DNA
```

<213> ORGANISM: Artificial Sequence
<220> FEATURE:
<223> OTHER INFORMATION: Description of Artificial Sequence: Synthetic
    polynucleotide
<220> FEATURE:
<223> OTHER INFORMATION: stuff sequence

<400> SEQUENCE: 7

```
cgtttaaggg caccaataac tgccttaaaa aaattacgcc ccgccctgcc actcatcgca      60
gtactgttgt aattcattaa gcattctgcc gacatggaag ccatcacaaa cggcatgatg     120
aacctgaatc gccagcggca tcagcacctt gtcgccttgc gtataatatt tgcccatagt     180
gaaaacgggg gcgaagaagt tgtccatatt ggccacgttt aaatcaaaac tggtgaaact     240
cacccaggga ttggctgaga cgaaaaacat attctcaata aacccttag ggaaataggc      300
caggttttca ccgtaacacg ccacatcttg cgaatatatg tgtagaaact gccgaaatc      360
gtcgtggtat tcactccaga gcgatgaaaa cgtttcagtt tgctcatgga aacggtgta      420
acaaggtga acactatccc atatcaccag ctcaccgtct ttcattgcca tacgaattc       480
cggatgagca ttcatcaggc gggcaagaat gtgaataaag gccggataaa acttgtgctt     540
attttttctt acggtcttta aaaggccgt aatatccagc tgaacggtct ggttataggt      600
acattgagca actgactgaa atgcctcaaa atgttcttta cgatgccatt gggatatatc     660
aacggtggta tatccagtga tttttttctc cacgtg                               696
```

<210> SEQ ID NO 8
<211> LENGTH: 132
<212> TYPE: PRT
<213> ORGANISM: Homo sapiens
<220> FEATURE:
<223> OTHER INFORMATION: human IL17

<400> SEQUENCE: 8

```
Gly Ile Thr Ile Pro Arg Asn Pro Gly Cys Pro Asn Ser Glu Asp Lys
1               5                   10                  15
Asn Phe Pro Arg Thr Val Met Val Asn Leu Asn Ile His Asn Arg Asn
            20                  25                  30
Thr Asn Thr Asn Pro Lys Arg Ser Ser Asp Tyr Tyr Asn Arg Ser Thr
        35                  40                  45
Ser Pro Trp Asn Leu His Arg Asn Glu Asp Pro Glu Arg Tyr Pro Ser
    50                  55                  60
Val Ile Trp Glu Ala Lys Cys Arg His Leu Gly Cys Ile Asn Ala Asp
65                  70                  75                  80
Gly Asn Val Asp Tyr His Met Asn Ser Val Pro Ile Gln Gln Glu Ile
                85                  90                  95
Leu Val Leu Arg Arg Glu Pro Pro His Cys Pro Asn Ser Phe Arg Leu
            100                 105                 110
Glu Lys Ile Leu Val Ser Val Gly Cys Thr Cys Val Thr Pro Ile Val
        115                 120                 125
His His Val Ala
    130
```

<210> SEQ ID NO 9
<211> LENGTH: 133
<212> TYPE: PRT
<213> ORGANISM: Mus musculus
<220> FEATURE:
<223> OTHER INFORMATION: mouse IL17

<400> SEQUENCE: 9

```
Ala Ile Ile Pro Gln Ser Ser Ala Cys Pro Asn Thr Glu Ala Lys
1               5                   10                  15

Asp Phe Leu Gln Asn Val Lys Val Asn Leu Lys Val Phe Asn Ser Leu
                20                  25                  30

Gly Ala Lys Val Ser Ser Arg Arg Pro Ser Asp Tyr Leu Asn Arg Ser
            35                  40                  45

Thr Ser Pro Trp Thr Leu His Arg Asn Glu Asp Pro Asp Arg Tyr Pro
    50                  55                  60

Ser Val Ile Trp Glu Ala Gln Cys Arg His Gln Arg Cys Val Asn Ala
65                  70                  75                  80

Glu Gly Lys Leu Asp His His Met Asn Ser Val Leu Ile Gln Gln Glu
                85                  90                  95

Ile Leu Val Leu Lys Arg Glu Pro Glu Ser Cys Pro Phe Thr Phe Arg
                100                 105                 110

Val Glu Lys Met Leu Val Gly Val Gly Cys Thr Cys Val Ala Ser Ile
            115                 120                 125

Val Arg Gln Ala Ala
        130

<210> SEQ ID NO 10
<211> LENGTH: 132
<212> TYPE: PRT
<213> ORGANISM: Macaca mulatta
<220> FEATURE:
<223> OTHER INFORMATION: Macaca mulatta IL17

<400> SEQUENCE: 10

Gly Ile Ala Ile Pro Arg Asn Pro Gly Cys Pro Asn Ser Glu Asp Lys
1               5                   10                  15

Thr Phe Pro Arg Thr Val Met Val Asn Leu Asn Ile His Asn Arg Asn
                20                  25                  30

Thr Asn Thr Asn Pro Lys Arg Ser Ser Asp Tyr Tyr Asn Arg Ser Thr
            35                  40                  45

Ser Pro Trp Asn Leu His Arg Asn Glu Asp Pro Glu Arg Tyr Pro Ser
    50                  55                  60

Val Ile Trp Glu Ala Lys Cys Arg His Leu Gly Cys Val Asn Ala Asp
65                  70                  75                  80

Gly Asn Val Asp Tyr His Met Asn Ser Val Pro Ile Gln Gln Glu Ile
                85                  90                  95

Leu Val Leu Arg Arg Glu Pro Arg His Cys Pro Asn Ser Phe Arg Leu
                100                 105                 110

Glu Lys Ile Leu Val Ser Val Gly Cys Thr Cys Val Thr Pro Ile Val
            115                 120                 125

His His Val Ala
        130

<210> SEQ ID NO 11
<211> LENGTH: 132
<212> TYPE: PRT
<213> ORGANISM: Macaca fascicularis
<220> FEATURE:
<223> OTHER INFORMATION: Macaca fascicularis IL17

<400> SEQUENCE: 11

Gly Ile Ala Ile Pro Arg Asn Ser Gly Cys Pro Asn Ser Glu Asp Lys
1               5                   10                  15

Asn Phe Pro Arg Thr Val Met Val Asn Leu Asn Ile His Asn Arg Asn
```

```
                    20                  25                  30
Thr Ser Thr Asn Pro Lys Arg Ser Ser Asp Tyr Tyr Asn Arg Ser Thr
                35                  40                  45
Ser Pro Trp Asn Leu His Arg Asn Glu Asp Pro Glu Arg Tyr Pro Ser
            50                  55                  60
Val Ile Trp Glu Ala Lys Cys Arg His Leu Gly Cys Val Lys Ala Asp
 65                  70                  75                  80
Gly Asn Val Asp Tyr His Met Asn Ser Val Pro Ile Gln Gln Glu Ile
                        85                  90                  95
Leu Val Leu Arg Arg Glu Pro Arg His Cys Pro Asn Ser Phe Arg Leu
                   100                 105                 110
Glu Lys Ile Leu Val Ser Val Gly Cys Thr Cys Val Thr Pro Ile Val
               115                 120                 125
His His Val Ala
           130

<210> SEQ ID NO 12
<211> LENGTH: 288
<212> TYPE: PRT
<213> ORGANISM: Homo sapiens
<220> FEATURE:
<223> OTHER INFORMATION: human IL17 receptor extracellular region

<400> SEQUENCE: 12

Leu Arg Leu Leu Asp His Arg Ala Leu Val Cys Ser Gln Pro Gly Leu
 1               5                  10                  15
Asn Cys Thr Val Lys Asn Ser Thr Cys Leu Asp Asp Ser Trp Ile His
                20                  25                  30
Pro Arg Asn Leu Thr Pro Ser Ser Pro Lys Asp Leu Gln Ile Gln Leu
                35                  40                  45
His Phe Ala His Thr Gln Gln Gly Asp Leu Phe Pro Val Ala His Ile
            50                  55                  60
Glu Trp Thr Leu Gln Thr Asp Ala Ser Ile Leu Tyr Leu Glu Gly Ala
 65                  70                  75                  80
Glu Leu Ser Val Leu Gln Leu Asn Thr Asn Glu Arg Leu Cys Val Arg
                    85                  90                  95
Phe Glu Phe Leu Ser Lys Leu Arg His His His Arg Arg Trp Arg Phe
                   100                 105                 110
Thr Phe Ser His Phe Val Val Asp Pro Asp Gln Glu Tyr Glu Val Thr
               115                 120                 125
Val His His Leu Pro Lys Pro Ile Pro Asp Gly Asp Pro Asn His Gln
           130                 135                 140
Ser Lys Asn Phe Leu Val Pro Asp Cys Glu His Ala Arg Met Lys Val
145                 150                 155                 160
Thr Thr Pro Cys Met Ser Ser Gly Ser Leu Trp Asp Pro Asn Ile Thr
                   165                 170                 175
Val Glu Thr Leu Glu Ala His Gln Leu Arg Val Ser Phe Thr Leu Trp
               180                 185                 190
Asn Glu Ser Thr His Tyr Gln Ile Leu Leu Thr Ser Phe Pro His Met
               195                 200                 205
Glu Asn His Ser Cys Phe Glu His Met His His Ile Pro Ala Pro Arg
           210                 215                 220
Pro Glu Glu Phe His Gln Arg Ser Asn Val Thr Leu Thr Leu Arg Asn
225                 230                 235                 240
Leu Lys Gly Cys Cys Arg His Gln Val Gln Ile Gln Pro Phe Phe Ser
```

```
                245                 250                 255
Ser Cys Leu Asn Asp Cys Leu Arg His Ser Ala Thr Val Ser Cys Pro
            260                 265                 270
Glu Met Pro Asp Thr Pro Glu Pro Ile Pro Asp Tyr Met Pro Leu Trp
        275                 280                 285

<210> SEQ ID NO 13
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: his tag

<400> SEQUENCE: 13

Ala Ser Gly Ala Ala His His His His His
1               5                   10

<210> SEQ ID NO 14
<211> LENGTH: 234
<212> TYPE: PRT
<213> ORGANISM: Homo sapiens
<220> FEATURE:
<223> OTHER INFORMATION: Fc tag

<400> SEQUENCE: 14

Ala Ser Glu Pro Lys Ser Ser Asp Lys Thr His Thr Cys Pro Pro Cys
1               5                   10                  15

Pro Ala Pro Glu Leu Leu Gly Gly Pro Ser Val Phe Leu Phe Pro Pro
            20                  25                  30

Lys Pro Lys Asp Thr Leu Met Ile Ser Arg Thr Pro Glu Val Thr Cys
        35                  40                  45

Val Val Val Asp Val Ser His Glu Asp Pro Glu Val Lys Phe Asn Trp
    50                  55                  60

Tyr Val Asp Gly Val Glu Val His Asn Ala Lys Thr Lys Pro Arg Glu
65                  70                  75                  80

Glu Gln Tyr Asn Ser Thr Tyr Arg Val Val Ser Val Leu Thr Val Leu
                85                  90                  95

His Gln Asp Trp Leu Asn Gly Lys Glu Tyr Lys Cys Lys Val Ser Asn
            100                 105                 110

Lys Ala Leu Pro Ala Pro Ile Glu Lys Thr Ile Ser Lys Ala Lys Gly
        115                 120                 125

Gln Pro Arg Glu Pro Gln Val Tyr Thr Leu Pro Pro Ser Arg Asp Glu
    130                 135                 140

Leu Thr Lys Asn Gln Val Ser Leu Thr Cys Leu Val Lys Gly Phe Tyr
145                 150                 155                 160

Pro Ser Asp Ile Ala Val Glu Trp Glu Ser Asn Gly Gln Pro Glu Asn
                165                 170                 175

Asn Tyr Lys Thr Thr Pro Pro Val Leu Asp Ser Asp Gly Ser Phe Phe
            180                 185                 190

Leu Tyr Ser Lys Leu Thr Val Asp Lys Ser Arg Trp Gln Gln Gly Asn
        195                 200                 205

Val Phe Ser Cys Ser Val Met His Glu Ala Leu His Asn His Tyr Thr
    210                 215                 220

Gln Lys Ser Leu Ser Leu Ser Pro Gly Lys
225                 230
```

<210> SEQ ID NO 15
<211> LENGTH: 747
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: single-chain antibody 11A

<400> SEQUENCE: 15

```
gaggtgcagc tggtggagtc tgggggaggc ttggtccagc ctgggggtc cctgagactc      60
tcctgtgcag cctctggatt cacctttagt gattactgga tgaattgggt ccgccaggct    120
ccagggaagg ggctggagtg ggtggccgca attaaccaaa gcggcgatga gaaatactat    180
gtgggctctg tgaagggccg attcaccatc tccagagaca acgccaagaa ctcactgtat    240
ctgcaaatga acagcctgag agtcgaggac acggctgtgt attactgtgt gagagactat    300
tacactttc tgagcgatta ttacatacac tactggtact cgatctctg gggccgtggc     360
accctggtca ctgtgtcctc aggtggtggt ggtagcggcg gcggcggctc tggtggtggt    420
ggatccgata tccagatgac ccagagcccg agcagcctga gcgcgagcgt gggtgatcgc    480
gtgaccatta cctgccgcgc gagccagagt atccgtaact acctgacttg gtatcagcag    540
aaacgggta aagcgccgaa actgttaatt tatggggcca gcagccggca gtctggcgtg    600
ccgtcgcgtt ttagcggctc gggttcgggc accgatttta ccctgaccat ctcgagcttg    660
cagccggagg acttcgccac ctactattgc cagcaatacg ccgggtcccc aatcaccttc    720
ggtcagggca ccaaagtgga gatcaaa                                         747
```

<210> SEQ ID NO 16
<211> LENGTH: 747
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: single-chain antibody 9G

<400> SEQUENCE: 16

```
gaggtgcagc tggtggagtc tgggggaggc ttggtccagc ctgggggtc cctgagactc      60
tcctgtgcag cctctggatt cacctttagt gattactgga tgaattgggt ccgccaggct    120
ccagggaagg ggctggagtg ggtggccgca attaaccaag acggcaatga gaaatactat    180
gtgggctctg tgaagggccg attcaccatc tccagagaca acgccaagaa ctcactgtat    240
ctgcaaatga acagcctgag agtcgaggac acggctgtgt attactgtgt gagagactat    300
tacgatgtga ttagcgatta ttacatacac tactggtact cgatctctg gggccgtggc     360
accctggtca ctgtgtcctc aggtggtggt ggtagcggcg gcggcggctc tggtggtggt    420
ggatccgata tccagatgac ccagagcccg agcagcctga gcgcgagcgt gggtgatcgc    480
gtgaccatta cctgccgcgc gagccaggat atccatagct acctgacttg gtatcagcag    540
aaacgggta aagcgccgaa actgttaatt tatggtgcca gcaccccggga gactggcgtg    600
ccgtcgcgtt ttagcggctc gggttcgggc accgatttta ccctgaccat ctcgagcttg    660
cagccggagg acttcgccac ctactattgc cagcaatacc gcggcacgcc aacgaccttc    720
ggtcagggca ccaaagtgga gatcaaa                                         747
```

<210> SEQ ID NO 17
<211> LENGTH: 318
<212> TYPE: DNA
<213> ORGANISM: Homo sapiens
<220> FEATURE:
<223> OTHER INFORMATION: Kappa light chain constant region of human
      antibody

<400> SEQUENCE: 17
gtggcggcgc catctgtctt catcttcccg ccatctgatg agcagttgaa atctggtacc      60
gctagcgttg tgtgcctgct gaataacttc tatcccagag aggccaaagt acagtggaag     120
gtggataacg ccctccaatc gggtaactcc caggagagtg tcacagagca ggacagcaag     180
gacagcacct acagcctcag cagcaccctg acgctgagca agcagacta cgagaaacac     240 aaagtctacg cctgcgaagt cacccatcag ggcctgagct cgcccgtcac aaagagcttc     300
aacaggggag agtgttag                                                   318

<210> SEQ ID NO 18
<211> LENGTH: 804
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Fusion gene of heavy chain constant region CH1
      of human antibody and C-terminal domain of gIII protein

<400> SEQUENCE: 18
gtgtcctcag cgtcgaccaa gggcccatcg gtcttccccc tggcaccctc ctccaagagc      60
acctctgggg gcacagcggc cctgggctgc ctggtcaagg actacttccc cgaaccggtg     120
acggtgtcgt ggaactcagg cgccctgacc agcggcgtgc acaccttccc ggctgtccta     180
cagtcctcag gactctactc cctcagcagc gtggtgaccg tgccctccag cagcttgggc     240
acccagacct acatctgcaa cgtgaatcac aagcccagca acaccaaggt ggacaagaga     300
gttgagccca atcttgtgc ggccgcaggt ggcggctccg gttccggtga ttttgattat     360
gaaaaaatgg caaacgctaa taaggggggct atgaccgaaa atgccgatga aaacgcgcta     420
cagtctgacg ctaaaggcaa acttgattct gtcgctactg attacggtgc tgctatcgat     480
ggtttcattg gtgacgtttc cggccttgct aatggtaatg gtgctactgg tgattttgct     540
ggctctaatt cccaaatggc tcaagtcggt gacggtgata attcaccttt aatgaataat     600
ttccgtcaat atttaccttc cctccctcaa tcggttgaat gtcgcccttt tgtctttggc     660
gctggtaaac catatgaatt ttctattgat tgtgacaaaa taaacttatt ccgtggtgtc     720
tttgcgtttc ttttatatgt tgccaccttt atgtatgtat tttctacgtt tgctaacata     780
ctgcgtaata aggagtcttg ataa                                            804

<210> SEQ ID NO 19
<211> LENGTH: 354
<212> TYPE: DNA
<213> ORGANISM: Homo sapiens
<220> FEATURE:
<223> OTHER INFORMATION: Lambda light chain constant region of human
      antibody

<400> SEQUENCE: 19
gtgctaggtc agcccaaggc tgccccctcg gtcactctgt tcccgccctc ctctgaggag      60
cttcaagcca acaaggccac actggtgtgt ctcataagtg acttctaccc gggagccgtg     120

```
acagtggcct ggaaggcaga tagcagcccc gtcaaggcgg agtgggagac caccacaccc      180
tccaaacaaa gcaacaacaa gtacgcggcc agcagctatc tgagcctgac gcctgagcag      240
tggaagtccc acagaagcta cagctgccag gtcacgcatg aagggagcac cgtggagaag      300
acagtggccc ctacagaatg ttcaggtgca gctcatcacc accatcacca ttaa            354

<210> SEQ ID NO 20
<211> LENGTH: 739
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: CDF ori

<400> SEQUENCE: 20
gcgctgcgga cacatacaaa gttacccaca gattccgtgg ataagcaggg gactaacatg      60
tgaggcaaaa cagcagggcc gcgccggtgg cgttttttcca taggctccgc cctcctgcca    120
gagttcacat aaacagacgc ttttccggtg catctgtggg agccgtgagg ctcaaccatg     180
aatctgacag tacgggcgaa acccgacagg acttaaagat ccccaccgtt tccggcgggt    240
cgctccctct tgcgctctcc tgttccgacc ctgccgttta ccggatacct gttccgcctt    300
tctcccttac gggaagtgtg gcgctttctc atagctcaca cactggtatc tcggctcgt     360 gtaggtcgtt cgctccaagc tgggctgtaa gcaagaactc cccgttcagc ccgactgctg    420
cgccttatcc ggtaactgtt cacttgagtc caacccggaa aagcacgta aaacgccact     480 ggcagcagcc attggtaact gggagttcgc agaggatttg tttagctaaa cacgcggttg    540
ctcttgaagt gtgcgccaaa gtccggctac actggaagga cagatttggt tgctgtgctc    600
tgcgaaaacc agttaccacg gttaagcagt tccccaactg acttaacctt cgatcaaacc    660
acctccccag gtggtttttt cgtttacagg gcaaaagatt acgcgcagaa aaaaggatc    720 tcaagaagat cctttgatc                                                739

<210> SEQ ID NO 21
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Antibody light chain

<400> SEQUENCE: 21

Asp Ile Gln Met Thr Gln Ser Pro Ser Ser Leu Ser Ala Ser Val Gly
1               5                  10                  15

Asp Arg Val Thr Ile Thr Cys Arg Ala Ser Gln Asn Val His Asn Arg
            20                  25                  30

Leu Thr Trp Tyr Gln Gln Lys Pro Gly Lys Ala Pro Lys Leu Leu Ile
        35                  40                  45

Tyr Gly Ala Ser Asn Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Gly Ser Pro Thr
                85                  90                  95

Thr Phe Gly Gln Gly Thr Lys Val Glu Ile Lys
```

<210> SEQ ID NO 22
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Antibody light chain

<400> SEQUENCE: 22

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asn Val Asn Asn Tyr
            20                  25                  30

Leu Thr Trp Tyr Gln Gln Lys Pro Gly Lys Ala Pro Lys Leu Leu Ile
        35                  40                  45

Tyr Gly Ala Ser Ser Arg Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Gly Ser Pro Thr
                85                  90                  95

Thr Phe Gly Gln Gly Thr Lys Val Glu Ile Lys
            100                 105

<210> SEQ ID NO 23
<211> LENGTH: 381
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Antibody heavy chain 9G

<400> SEQUENCE: 23
gaggtgcagc tggtggagtc tgggggaggc ttggtccagc ctggggggtc cctgagactc      60
tcctgtgcag cctctggatt cacctttagt gattactgga tgaattgggt ccgccaggct     120
ccagggaagg ggctggagtg ggtggccgca attaaccaag acggcaatga aaatactat     180 gtgggctctg tgaagggccg attcaccatc tccagagaca acgccaagaa ctcactgtat     240
ctgcaaatga acagcctgag agtcgaggac acggctgtgt attactgtgt gagagactat     300
tacgatgtga ttagcgatta ttacatacac tactggtact cgatctctg gggccgtggc     360 accctggtca ctgtgtcctc a                                                381

<210> SEQ ID NO 24
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Antibody heavy chain

<400> SEQUENCE: 24

Glu Val Gln Leu Val Glu Ser Gly Gly Gly Leu Val Gln Pro Gly Gly
1               5                   10                  15

-continued

```
Ser Leu Arg Leu Ser Cys Ala Ala Ser Gly Ile Thr Met Asp Asp Tyr
            20                  25                  30

Trp Met Asn Trp Val Arg Gln Ala Pro Gly Lys Gly Leu Glu Trp Val
        35                  40                  45

Ala Ala Ile Asn Gln Asp Gly Asn Glu Lys Tyr Tyr Val Gly Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Val Glu Asp Thr Ala Val Tyr Tyr Cys
                85                  90                  95

Val Arg Asp Tyr Tyr Asp Leu Ile Ser Asp Tyr Tyr Ile His Tyr Trp
            100                 105                 110

Tyr Phe Asp Leu Trp Gly Arg Gly Thr Leu Val Thr Val Ser Ser
            115                 120                 125

<210> SEQ ID NO 25
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Antibody heavy chain

<400> SEQUENCE: 25

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Ile Asp Asn Tyr
            20                  25                  30

Trp Met Asn Trp Val Arg Gln Ala Pro Gly Lys Gly Leu Glu Trp Val
        35                  40                  45

Ala Ala Ile Asn Gln Asp Gly Asn Glu Lys Tyr Tyr Val Gly Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Val Glu Asp Thr Ala Val Tyr Tyr Cys
                85                  90                  95

Val Arg Asp Tyr Tyr Asp Val Ile Ser Asp Tyr Tyr Ile His Tyr Trp
            100                 105                 110

Tyr Phe Asp Leu Trp Gly Arg Gly Thr Leu Val Thr Val Ser Ser
            115                 120                 125

<210> SEQ ID NO 26
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Antibody heavy chain

<400> SEQUENCE: 26

Glu Val Gln Leu Val Glu Ser Gly Gly Gly Leu Val Gln Pro Gly Gly
1               5                   10                  15

Ser Leu Arg Leu Ser Cys Ala Ala Ser Gly Met Ser Met Ser Asp Tyr
            20                  25                  30

Trp Met Asn Trp Val Arg Gln Ala Pro Gly Lys Gly Leu Glu Trp Val
        35                  40                  45
```

```
Ala Ala Ile Asn Gln Asp Gly Asp Glu Lys Tyr Tyr Val Gly Ser Val
            50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Val Glu Asp Thr Ala Val Tyr Tyr Cys
                 85                  90                  95

Val Arg Asp Tyr Tyr Asp Leu Ile Ser Asp Tyr Tyr Ile His Tyr Trp
                100                 105                 110

Tyr Phe Asp Leu Trp Gly Arg Gly Thr Leu Val Thr Val Ser Ser
                115                 120                 125

<210> SEQ ID NO 27
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: VH

<400> SEQUENCE: 27

Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Ser Asn Tyr
                 20                  25                  30

Trp Met Asn Trp Val Arg Gln Ala Pro Gly Lys Gly Leu Glu Trp Val
             35                  40                  45

Ala Ala Ile Asn Gln Asp Gly Ser Glu Lys Tyr Tyr Val Gly Ser Val
            50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Val Glu Asp Thr Ala Val Tyr Tyr Cys
                 85                  90                  95

Val Arg Asp Tyr Tyr Asp Ile Leu Thr Asp Tyr Tyr Ile His Tyr Trp
                100                 105                 110

Tyr Phe Asp Leu Trp Gly Arg Gly Thr Leu Val Thr Val Ser Ser
                115                 120                 125

<210> SEQ ID NO 28
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: VK

<400> SEQUENCE: 28

Glu Ile Val Leu Thr Gln Ser Pro Gly Thr Leu Ser Leu Ser Pro Gly
  1               5                  10                  15

Glu Arg Ala Thr Leu Ser Cys Arg Ala Ser Gln Ser Val Ser Ser Ser
                 20                  25                  30

Tyr Leu Ala Trp Tyr Gln Gln Lys Pro Gly Gln Ala Pro Arg Leu Leu
             35                  40                  45

Ile Tyr Gly Ala Ser Ser Arg Ala Thr Gly Ile Pro Asp Arg Phe Ser
         50                  55                  60

Gly Ser Gly Ser Gly Thr Asp Phe Thr Leu Thr Ile Ser Arg Leu Glu
```

```
                65                  70                  75                  80
Pro Glu Asp Phe Ala Val Tyr Tyr Cys Gln Gln Tyr Gly Ser Ser Pro
                    85                  90                  95
Cys Thr Phe Gly Gln Gly Thr Arg Leu Glu Ile Lys
                100                 105

<210> SEQ ID NO 29
<211> LENGTH: 330
<212> TYPE: PRT
<213> ORGANISM: Homo sapiens
<220> FEATURE:
<223> OTHER INFORMATION: IgG1 subtype of antibody heavy chain constant
      region

<400> SEQUENCE: 29

Ala Ser Thr Lys Gly Pro Ser Val Phe Pro Leu Ala Pro Ser Ser Lys
1               5                   10                  15
Ser Thr Ser Gly Gly Thr Ala Ala Leu Gly Cys Leu Val Lys Asp Tyr
                20                  25                  30
Phe Pro Glu Pro Val Thr Val Ser Trp Asn Ser Gly Ala Leu Thr Ser
                35                  40                  45
Gly Val His Thr Phe Pro Ala Val Leu Gln Ser Ser Gly Leu Tyr Ser
            50                  55                  60
Leu Ser Ser Val Val Thr Val Pro Ser Ser Ser Leu Gly Thr Gln Thr
65                  70                  75                  80
Tyr Ile Cys Asn Val Asn His Lys Pro Ser Asn Thr Lys Val Asp Lys
                85                  90                  95
Arg Val Glu Pro Lys Ser Cys Asp Lys Thr His Thr Cys Pro Pro Cys
                100                 105                 110
Pro Ala Pro Glu Leu Leu Gly Gly Pro Ser Val Phe Leu Phe Pro Pro
            115                 120                 125
Lys Pro Lys Asp Thr Leu Met Ile Ser Arg Thr Pro Glu Val Thr Cys
130                 135                 140
Val Val Val Asp Val Ser His Glu Asp Pro Glu Val Lys Phe Asn Trp
145                 150                 155                 160
Tyr Val Asp Gly Val Glu Val His Asn Ala Lys Thr Lys Pro Arg Glu
                165                 170                 175
Glu Gln Tyr Asn Ser Thr Tyr Arg Val Val Ser Val Leu Thr Val Leu
                180                 185                 190
His Gln Asp Trp Leu Asn Gly Lys Glu Tyr Lys Cys Lys Val Ser Asn
            195                 200                 205
Lys Ala Leu Pro Ala Pro Ile Glu Lys Thr Ile Ser Lys Ala Lys Gly
            210                 215                 220
Gln Pro Arg Glu Pro Gln Val Tyr Thr Leu Pro Pro Ser Arg Glu Glu
225                 230                 235                 240
Met Thr Lys Asn Gln Val Ser Leu Thr Cys Leu Val Lys Gly Phe Tyr
                245                 250                 255
Pro Ser Asp Ile Ala Val Glu Trp Glu Ser Asn Gly Gln Pro Glu Asn
                260                 265                 270
Asn Tyr Lys Thr Thr Pro Pro Val Leu Asp Ser Asp Gly Ser Phe Phe
            275                 280                 285
Leu Tyr Ser Lys Leu Thr Val Asp Lys Ser Arg Trp Gln Gln Gly Asn
            290                 295                 300
Val Phe Ser Cys Ser Val Met His Glu Ala Leu His Asn His Tyr Thr
305                 310                 315                 320
```

Gln Lys Ser Leu Ser Leu Ser Pro Gly Lys
                325                 330

<210> SEQ ID NO 30
<211> LENGTH: 327
<212> TYPE: PRT
<213> ORGANISM: Homo sapiens
<220> FEATURE:
<223> OTHER INFORMATION: IgG4 subtype of antibody heavy chain constant
      region

<400> SEQUENCE: 30

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 31

```
<211> LENGTH: 107
<212> TYPE: PRT
<213> ORGANISM: Homo sapiens
<220> FEATURE:
<223> OTHER INFORMATION: Kappa subtype light chain constant region

<400> SEQUENCE: 31

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 32
<211> LENGTH: 105
<212> TYPE: PRT
<213> ORGANISM: Homo sapiens
<220> FEATURE:
<223> OTHER INFORMATION: Lambda subtype light chain constant region

<400> SEQUENCE: 32

Gln Pro Lys Ala Ala Pro Ser Val Thr Leu Phe Pro Pro Ser Ser Glu
1               5                   10                  15

Glu Leu Gln Ala Asn Lys Ala Thr Leu Val Cys Leu Ile Ser Asp Phe
            20                  25                  30

Tyr Pro Gly Ala Val Thr Val Ala Trp Lys Ala Asp Ser Ser Pro Val
        35                  40                  45

Lys Ala Gly Val Glu Thr Thr Thr Pro Ser Lys Gln Ser Asn Asn Lys
    50                  55                  60

Tyr Ala Ala Ser Ser Tyr Leu Ser Leu Thr Pro Glu Gln Trp Lys Ser
65                  70                  75                  80

His Arg Ser Tyr Ser Cys Gln Val Thr His Glu Gly Ser Thr Val Glu
                85                  90                  95

Lys Thr Val Ala Pro Thr Glu Cys Ser
            100                 105

<210> SEQ ID NO 33
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: VH

<400> SEQUENCE: 33

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ser Phe Thr Asp Tyr
            20                  25                  30
```

```
His Ile His Trp Val Arg Gln Ala Pro Gly Gln Gly Leu Glu Trp Met
            35                  40                  45

Gly Val Ile Asn Pro Met Tyr Gly Thr Thr Asp Tyr Asn Gln Arg Phe
 50                  55                  60

Lys Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Tyr Asp Tyr Phe Thr Gly Thr Gly Val Tyr Trp Gly Gln Gly
                100                 105                 110

Thr Leu Val Thr Val Ser Ser
           115
```

<210> SEQ ID NO 34
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: VK

<400> SEQUENCE: 34

```
Asp Ile Val Met Thr Gln Thr Pro Leu Ser Leu Ser Val Thr Pro Gly
 1               5                  10                  15

Gln Pro Ala Ser Ile Ser Cys Arg Ser Ser Arg Ser Leu Val His Ser
             20                  25                  30

Arg Gly Asn Thr Tyr Leu His Trp Tyr Leu Gln Lys Pro Gly Gln Ser
         35                  40                  45

Pro Gln Leu Leu Ile Tyr Lys Val Ser Asn Arg Phe Ile Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Ser Gln Ser
                 85                  90                  95

Thr His Leu Pro Phe Thr Phe Gly Gln Gly Thr Lys Leu Glu Ile Lys
                100                 105                 110
```

<210> SEQ ID NO 35
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Asn or Asp

<400> SEQUENCE: 35

```
Asn Gln Asp Gly Xaa Glu
 1               5
```

<210> SEQ ID NO 36
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:

```
<221> NAME/KEY: MOD_RES
<222> LOCATION: (5)..(5)
<223> OTHER INFORMATION: Val or Leu

<400> SEQUENCE: 36

Asp Tyr Tyr Asp Xaa Ile Ser Asp Tyr Tyr Ile His Tyr Trp Tyr Phe
1               5                   10                  15

Asp Leu

<210> SEQ ID NO 37
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Phe Thr Ile Asp Asn
1               5

<210> SEQ ID NO 38
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Met Ser Met Ser Asp
1               5

<210> SEQ ID NO 39
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Ile Thr Met Asp Asp
1               5

<210> SEQ ID NO 40
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Arg Ala Ser Gln Asn Val His Asn Arg Leu Thr
1               5                   10

<210> SEQ ID NO 41
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Gly Ala Ser Asn Leu Glu Ser
```

<210> SEQ ID NO 42
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Gln Gln Tyr Asn Gly Ser Pro Thr Thr
1               5

<210> SEQ ID NO 43
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
cagrtgcagc tggtgcartc tgg                                              23

<210> SEQ ID NO 44
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
saggtccagc tggtrcagtc tgg                                              23

<210> SEQ ID NO 45
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
cagrtcacct tgaaggagtc tgg                                              23

<210> SEQ ID NO 46
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
saggtgcagc tggtggagtc tgg                                              23

<210> SEQ ID NO 47
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
gaggtgcagc tggtggagwc ygg    23

<210> SEQ ID NO 48
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
caggtgcagc tacagcagtg ggg    23

<210> SEQ ID NO 49
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
cagstgcagc tgcaggagtc sgg    23

<210> SEQ ID NO 50
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
gargtgcagc tggtgcagtc tgg    23

<210> SEQ ID NO 51
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
caggtacagc tgcagcagtc agg    23

<210> SEQ ID NO 52
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
tgaggagacg gtgaccaggg tgcc    24

<210> SEQ ID NO 53
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
tgaagagacg gtgaccattg tccc    24

<210> SEQ ID NO 54
<211> LENGTH: 24
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 54
tgaggagacg gtgaccaggg ttcc                                          24

<210> SEQ ID NO 55
<211> LENGTH: 24
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 55
tgaggagacg gtgaccgtgg tccc                                          24

<210> SEQ ID NO 56
<211> LENGTH: 23
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 56
gacatccagw tgacccagtc tcc                                           23

<210> SEQ ID NO 57
<211> LENGTH: 23
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 57
gatgttgtga tgactcagtc tcc                                           23

<210> SEQ ID NO 58
<211> LENGTH: 23
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 58
gaaattgtgw tgacrcagtc tcc                                           23

<210> SEQ ID NO 59
<211> LENGTH: 23
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 59
gatattgtga tgacccagac tcc                                           23

<210> SEQ ID NO 60
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
gaaacgacac tcacgcagtc tcc                                           23

<210> SEQ ID NO 61
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61
gaaattgtgc tgactcagtc tcc                                           23

<210> SEQ ID NO 62
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 62
acgtttgatc tcgagcttgg tcccytggcc raa                                33

<210> SEQ ID NO 63
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 63
acgtttgatc tcgagtttgg tcccagggcc gaa                                33

<210> SEQ ID NO 64
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 64
acgtttgatc tcgagcttgg tccctccgcc gaa                                33

<210> SEQ ID NO 65
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 65
acgtttaatc tcgagtcgtg tcccttggcc gaa                                33

<210> SEQ ID NO 66
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 66
cagtctgtgy tgackcagcc rcc          23

<210> SEQ ID NO 67
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 67
cartctgccc tgactcagcc t            21

<210> SEQ ID NO 68
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 68
tcctatgwgc tgactcagcc a            21

<210> SEQ ID NO 69
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 69
tcttctgagc tgactcagga ccc          23

<210> SEQ ID NO 70
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 70
caggctgtgc tgactcagcc g            21

<210> SEQ ID NO 71
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 71
aattttatgc tgactcagcc cca          23

<210> SEQ ID NO 72

```
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 72
cagrctgtgg tgacycagga gcc                                          23

<210> SEQ ID NO 73
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 73
cwgcctgtgc tgactcagcc                                              20

<210> SEQ ID NO 74
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 74
acctaggacg gtgaccttgg tccc                                         24

<210> SEQ ID NO 75
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 75
acctaggacg gtcagcttgg tccc                                         24

<210> SEQ ID NO 76
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 76
acctaaaacg gtgagctggg tccc                                         24

<210> SEQ ID NO 77
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 77
actagctagc gcgcaggtgc agttagtgca gag                               33

<210> SEQ ID NO 78
<211> LENGTH: 51
```

<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (21)..(21)
<223> OTHER INFORMATION: a, c, t, g, unknown or other

<400> SEQUENCE: 78
ggtgcctgac gcacccaryk natrkmatar yyrstaaagg tgccgccact c            51

<210> SEQ ID NO 79
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 79
gcccatccat tccaggccct gtcccggtgc ctgacgcacc ca                      42

<210> SEQ ID NO 80
<211> LENGTH: 69
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (26)..(26)
<223> OTHER INFORMATION: a, c, t, g, unknown or other
<220> FEATURE:
<221> NAME/KEY: modified_base
<222> LOCATION: (45)..(45)
<223> OTHER INFORMATION: a, c, t, g, unknown or other
<220> FEATURE:
<221> NAME/KEY: modified_base
<222> LOCATION: (48)..(48)
<223> OTHER INFORMATION: a, c, t, g, unknown or other

<400> SEQUENCE: 80
ggcctggaat ggatgggckg gataanyccg wwytyyggcr vyrcnaanta tgcgcagaaa   60
ttccaaggc                                                           69

<210> SEQ ID NO 81
<211> LENGTH: 64
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (22)..(23)
<223> OTHER INFORMATION: a, c, t, g, unknown or other
<220> FEATURE:
<221> NAME/KEY: modified_base
<222> LOCATION: (25)..(26)
<223> OTHER INFORMATION: a, c, t, g, unknown or other
<220> FEATURE:
<221> NAME/KEY: modified_base
<222> LOCATION: (28)..(29)
<223> OTHER INFORMATION: a, c, t, g, unknown or other
<220> FEATURE:
<221> NAME/KEY: modified_base
<222> LOCATION: (31)..(32)
<223> OTHER INFORMATION: a, c, t, g, unknown or other
<220> FEATURE:

<221> NAME/KEY: modified_base
<222> LOCATION: (34)..(35)
<223> OTHER INFORMATION: a, c, t, g, unknown or other
<220> FEATURE:
<221> NAME/KEY: modified_base
<222> LOCATION: (37)..(38)
<223> OTHER INFORMATION: a, c, t, g, unknown or other
<220> FEATURE:
<221> NAME/KEY: modified_base
<222> LOCATION: (40)..(41)
<223> OTHER INFORMATION: a, c, t, g, unknown or other
<220> FEATURE:
<221> NAME/KEY: modified_base
<222> LOCATION: (43)..(43)
<223> OTHER INFORMATION: a, c, t, g, unknown or other

<400> SEQUENCE: 81
gtgccctggc cccaatagtc snnsnnsnns nnsnnsnnsn nsnbacgggc gcaataatac    60
acag                                                                64

<210> SEQ ID NO 82
<211> LENGTH: 70
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (23)..(23)
<223> OTHER INFORMATION: a, c, t, g, unknown or other
<220> FEATURE:
<221> NAME/KEY: modified_base
<222> LOCATION: (26)..(26)
<223> OTHER INFORMATION: a, c, t, g, unknown or other
<220> FEATURE:
<221> NAME/KEY: modified_base
<222> LOCATION: (29)..(29)
<223> OTHER INFORMATION: a, c, t, g, unknown or other
<220> FEATURE:
<221> NAME/KEY: modified_base
<222> LOCATION: (31)..(32)
<223> OTHER INFORMATION: a, c, t, g, unknown or other
<220> FEATURE:
<221> NAME/KEY: modified_base
<222> LOCATION: (34)..(35)
<223> OTHER INFORMATION: a, c, t, g, unknown or other
<220> FEATURE:
<221> NAME/KEY: modified_base
<222> LOCATION: (37)..(38)
<223> OTHER INFORMATION: a, c, t, g, unknown or other
<220> FEATURE:
<221> NAME/KEY: modified_base
<222> LOCATION: (40)..(41)
<223> OTHER INFORMATION: a, c, t, g, unknown or other
<220> FEATURE:
<221> NAME/KEY: modified_base
<222> LOCATION: (43)..(44)
<223> OTHER INFORMATION: a, c, t, g, unknown or other
<220> FEATURE:
<221> NAME/KEY: modified_base
<222> LOCATION: (46)..(46)
<223> OTHER INFORMATION: a, c, t, g, unknown or other
<220> FEATURE:
<221> NAME/KEY: modified_base
<222> LOCATION: (49)..(49)
<223> OTHER INFORMATION: a, c, t, g, unknown or other

<400> SEQUENCE: 82
gtgccctggc cccaatagtc srnsbnsyns nnsnnsnnsn nsnnsnbsnb acgggcgcaa    60
taatacacag                                                          70

<210> SEQ ID NO 83

<211> LENGTH: 76
<212> TYPE: DNA
<213> ORGANISM: Artificial Sequence
<220> FEATURE:
<223> OTHER INFORMATION: Description of Artificial Sequence: Synthetic primer
<220> FEATURE:
<221> NAME/KEY: modified_base
<222> LOCATION: (25)..(26)
<223> OTHER INFORMATION: a, c, t, g, unknown or other
<220> FEATURE:
<221> NAME/KEY: modified_base
<222> LOCATION: (28)..(29)
<223> OTHER INFORMATION: a, c, t, g, unknown or other
<220> FEATURE:
<221> NAME/KEY: modified_base
<222> LOCATION: (31)..(32)
<223> OTHER INFORMATION: a, c, t, g, unknown or other
<220> FEATURE:
<221> NAME/KEY: modified_base
<222> LOCATION: (34)..(35)
<223> OTHER INFORMATION: a, c, t, g, unknown or other
<220> FEATURE:
<221> NAME/KEY: modified_base
<222> LOCATION: (37)..(38)
<223> OTHER INFORMATION: a, c, t, g, unknown or other
<220> FEATURE:
<221> NAME/KEY: modified_base
<222> LOCATION: (40)..(41)
<223> OTHER INFORMATION: a, c, t, g, unknown or other
<220> FEATURE:
<221> NAME/KEY: modified_base
<222> LOCATION: (43)..(44)
<223> OTHER INFORMATION: a, c, t, g, unknown or other
<220> FEATURE:
<221> NAME/KEY: modified_base
<222> LOCATION: (46)..(47)
<223> OTHER INFORMATION: a, c, t, g, unknown or other
<220> FEATURE:
<221> NAME/KEY: modified_base
<222> LOCATION: (49)..(50)
<223> OTHER INFORMATION: a, c, t, g, unknown or other
<220> FEATURE:
<221> NAME/KEY: modified_base
<222> LOCATION: (52)..(53)
<223> OTHER INFORMATION: a, c, t, g, unknown or other
<220> FEATURE:
<221> NAME/KEY: modified_base
<222> LOCATION: (55)..(55)
<223> OTHER INFORMATION: a, c, t, g, unknown or other

<400> SEQUENCE: 83
gtgccctggc cccaatagtc gaasnnsnns nnsnnrnnsn nrnnsnnsnn snnsnbacgg    60
gcgcaataat acacag                                                   76

<210> SEQ ID NO 84
<211> LENGTH: 50
<212> TYPE: DNA
<213> ORGANISM: Artificial Sequence
<220> FEATURE:
<223> OTHER INFORMATION: Description of Artificial Sequence: Synthetic primer

<400> SEQUENCE: 84
tcatagcggc cgcagatgac acagtcacca gggtgccctg gccccaatag              50

<210> SEQ ID NO 85
<211> LENGTH: 34
<212> TYPE: DNA
<213> ORGANISM: Artificial Sequence
<220> FEATURE:
<223> OTHER INFORMATION: Description of Artificial Sequence: Synthetic primer

<400> SEQUENCE: 85
tcatagcggc cgccgcggtg ctggtagatt tgtc    34

<210> SEQ ID NO 86
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 86
atagctagcg cggaagtgca attggtggaa agc    33

<210> SEQ ID NO 87
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 87
gtgcctggcg cacccarykc atcsmgtarb ygctaaaggt gaagccgctc    50

<210> SEQ ID NO 88
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 88
gtgcctggcg cacccatgac atcsmgtagc tgctaaaggt gaagcc    46

<210> SEQ ID NO 89
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 89
gtgcctggcg cacccagtgc atcsmgtagc tgctaaaggt gaagcc    46

<210> SEQ ID NO 90
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 90
cacccattcc agacctttac ccggtgcctg gcgcaccca    39

<210> SEQ ID NO 91
<211> LENGTH: 73
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (33)..(33)
<223> OTHER INFORMATION: a, c, t, g, unknown or other

<400> SEQUENCE: 91
ggtaaaggtc tggaatgggt gkcmkkyatt arnkvyrryg gcrrywmyam rtactatgcg    60
gatagcgtga aag                                                      73

<210> SEQ ID NO 92
<211> LENGTH: 64
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (24)..(25)
<223> OTHER INFORMATION: a, c, t, g, unknown or other
<220> FEATURE:
<221> NAME/KEY: modified_base
<222> LOCATION: (27)..(28)
<223> OTHER INFORMATION: a, c, t, g, unknown or other
<220> FEATURE:
<221> NAME/KEY: modified_base
<222> LOCATION: (30)..(31)
<223> OTHER INFORMATION: a, c, t, g, unknown or other
<220> FEATURE:
<221> NAME/KEY: modified_base
<222> LOCATION: (33)..(34)
<223> OTHER INFORMATION: a, c, t, g, unknown or other
<220> FEATURE:
<221> NAME/KEY: modified_base
<222> LOCATION: (36)..(37)
<223> OTHER INFORMATION: a, c, t, g, unknown or other
<220> FEATURE:
<221> NAME/KEY: modified_base
<222> LOCATION: (39)..(40)
<223> OTHER INFORMATION: a, c, t, g, unknown or other

<400> SEQUENCE: 92
tgccctgacc ccagtaatcm adsnnsnnrn nsnnsnnrnn sbbyyttgcg caataataca    60
ccgc                                                                64

<210> SEQ ID NO 93
<211> LENGTH: 70
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (25)..(25)
<223> OTHER INFORMATION: a, c, t, g, unknown or other
<220> FEATURE:
<221> NAME/KEY: modified_base
<222> LOCATION: (28)..(28)
<223> OTHER INFORMATION: a, c, t, g, unknown or other
<220> FEATURE:
<221> NAME/KEY: modified_base
<222> LOCATION: (31)..(31)
<223> OTHER INFORMATION: a, c, t, g, unknown or other
<220> FEATURE:
<221> NAME/KEY: modified_base
<222> LOCATION: (34)..(34)
<223> OTHER INFORMATION: a, c, t, g, unknown or other
<220> FEATURE:
<221> NAME/KEY: modified_base
<222> LOCATION: (37)..(37)
<223> OTHER INFORMATION: a, c, t, g, unknown or other
<220> FEATURE:
<221> NAME/KEY: modified_base
<222> LOCATION: (40)..(40)

```
<223> OTHER INFORMATION: a, c, t, g, unknown or other
<220> FEATURE:
<221> NAME/KEY: modified_base
<222> LOCATION: (43)..(43)
<223> OTHER INFORMATION: a, c, t, g, unknown or other
<220> FEATURE:
<221> NAME/KEY: modified_base
<222> LOCATION: (46)..(47)
<223> OTHER INFORMATION: a, c, t, g, unknown or other

<400> SEQUENCE: 93
tgccctgacc ccagtaatcm adssnssnss nssnssnssn ssnssnnyyy yttgcgcaat     60
aatacaccgc                                                           70

<210> SEQ ID NO 94
<211> LENGTH: 76
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (24)..(25)
<223> OTHER INFORMATION: a, c, t, g, unknown or other
<220> FEATURE:
<221> NAME/KEY: modified_base
<222> LOCATION: (30)..(31)
<223> OTHER INFORMATION: a, c, t, g, unknown or other
<220> FEATURE:
<221> NAME/KEY: modified_base
<222> LOCATION: (33)..(34)
<223> OTHER INFORMATION: a, c, t, g, unknown or other
<220> FEATURE:
<221> NAME/KEY: modified_base
<222> LOCATION: (36)..(37)
<223> OTHER INFORMATION: a, c, t, g, unknown or other
<220> FEATURE:
<221> NAME/KEY: modified_base
<222> LOCATION: (39)..(40)
<223> OTHER INFORMATION: a, c, t, g, unknown or other
<220> FEATURE:
<221> NAME/KEY: modified_base
<222> LOCATION: (42)..(43)
<223> OTHER INFORMATION: a, c, t, g, unknown or other
<220> FEATURE:
<221> NAME/KEY: modified_base
<222> LOCATION: (45)..(46)
<223> OTHER INFORMATION: a, c, t, g, unknown or other
<220> FEATURE:
<221> NAME/KEY: modified_base
<222> LOCATION: (49)..(49)
<223> OTHER INFORMATION: a, c, t, g, unknown or other
<220> FEATURE:
<221> NAME/KEY: modified_base
<222> LOCATION: (51)..(53)
<223> OTHER INFORMATION: a, c, t, g, unknown or other

<400> SEQUENCE: 94
tgccctgacc ccagtaatcm adsnnrymsn nsnnsnnsnn snnsnnrdnr nnnyyybttg     60
cgcaataata caccgc                                                    76

<210> SEQ ID NO 95
<211> LENGTH: 52
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 95
tcatagcggc cgcgctcgac acggtcacca gagtgccctg accccagtaa tc             52
```

<210> SEQ ID NO 96
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 96
cagccatggc cgaagttc                                                     18

<210> SEQ ID NO 97
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 97
cygatccagt agbtggtgaa wstataacca gagcctttgc ag                          42

<210> SEQ ID NO 98
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 98
ctggcatctg gcgaacccaa cygatccagt agbtggtgaa                             40

<210> SEQ ID NO 99
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 99
tacccatcca ttccagacct ttgcctggca tctggcgaac c                           41

<210> SEQ ID NO 100
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 100
acccargtga cagcdacacc avwtattctc caagcttcca ggg                         43

<210> SEQ ID NO 101
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 101
ggtctggaat ggatgggtak aattdaccca rgtgacagcd acac                        44

```
<210> SEQ ID NO 102
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 102
ctaagcggcc gcgcgtgcac aatagtacat agc                                    33

<210> SEQ ID NO 103
<211> LENGTH: 67
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (30)..(31)
<223> OTHER INFORMATION: a, c, t, g, unknown or other
<220> FEATURE:
<221> NAME/KEY: modified_base
<222> LOCATION: (33)..(34)
<223> OTHER INFORMATION: a, c, t, g, unknown or other
<220> FEATURE:
<221> NAME/KEY: modified_base
<222> LOCATION: (36)..(37)
<223> OTHER INFORMATION: a, c, t, g, unknown or other
<220> FEATURE:
<221> NAME/KEY: modified_base
<222> LOCATION: (39)..(40)
<223> OTHER INFORMATION: a, c, t, g, unknown or other
<220> FEATURE:
<221> NAME/KEY: modified_base
<222> LOCATION: (42)..(43)
<223> OTHER INFORMATION: a, c, t, g, unknown or other

<400> SEQUENCE: 103
ccagagtacc ttgaccccaa drgkmgwrsn nsnnsnnsnn snnghsgcgt gcacaatagt        60
acatagc                                                                 67

<210> SEQ ID NO 104
<211> LENGTH: 63
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (21)..(21)
<223> OTHER INFORMATION: a, c, t, g, unknown or other
<220> FEATURE:
<221> NAME/KEY: modified_base
<222> LOCATION: (24)..(24)
<223> OTHER INFORMATION: a, c, t, g, unknown or other
<220> FEATURE:
<221> NAME/KEY: modified_base
<222> LOCATION: (26)..(27)
<223> OTHER INFORMATION: a, c, t, g, unknown or other
<220> FEATURE:
<221> NAME/KEY: modified_base
<222> LOCATION: (32)..(33)
<223> OTHER INFORMATION: a, c, t, g, unknown or other
<220> FEATURE:
<221> NAME/KEY: modified_base
<222> LOCATION: (35)..(36)
<223> OTHER INFORMATION: a, c, t, g, unknown or other
<220> FEATURE:
<221> NAME/KEY: modified_base
<222> LOCATION: (38)..(38)
```

<223> OTHER INFORMATION: a, c, t, g, unknown or other
<220> FEATURE:
<221> NAME/KEY: modified_base
<222> LOCATION: (41)..(41)
<223> OTHER INFORMATION: a, c, t, g, unknown or other

<400> SEQUENCE: 104
ttgaccccag daatcgaagd nahnsnnavc snnsnntnss nbgcgtgcac aatagtacat    60
agc    63

<210> SEQ ID NO 105
<211> LENGTH: 66
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (23)..(24)
<223> OTHER INFORMATION: a, c, t, g, unknown or other
<220> FEATURE:
<221> NAME/KEY: modified_base
<222> LOCATION: (26)..(27)
<223> OTHER INFORMATION: a, c, t, g, unknown or other
<220> FEATURE:
<221> NAME/KEY: modified_base
<222> LOCATION: (32)..(32)
<223> OTHER INFORMATION: a, c, t, g, unknown or other
<220> FEATURE:
<221> NAME/KEY: modified_base
<222> LOCATION: (35)..(36)
<223> OTHER INFORMATION: a, c, t, g, unknown or other
<220> FEATURE:
<221> NAME/KEY: modified_base
<222> LOCATION: (38)..(39)
<223> OTHER INFORMATION: a, c, t, g, unknown or other
<220> FEATURE:
<221> NAME/KEY: modified_base
<222> LOCATION: (41)..(42)
<223> OTHER INFORMATION: a, c, t, g, unknown or other
<220> FEATURE:
<221> NAME/KEY: modified_base
<222> LOCATION: (44)..(45)
<223> OTHER INFORMATION: a, c, t, g, unknown or other

<400> SEQUENCE: 105
ttgaccccag taatcgaagt asnnsnnabh wnbanngnna nnsnngcgtg cacaatagta    60
catagc    66

<210> SEQ ID NO 106
<211> LENGTH: 72
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (24)..(24)
<223> OTHER INFORMATION: a, c, t, g, unknown or other
<220> FEATURE:
<221> NAME/KEY: modified_base
<222> LOCATION: (26)..(27)
<223> OTHER INFORMATION: a, c, t, g, unknown or other
<220> FEATURE:
<221> NAME/KEY: modified_base
<222> LOCATION: (30)..(30)
<223> OTHER INFORMATION: a, c, t, g, unknown or other
<220> FEATURE:
<221> NAME/KEY: modified_base
<222> LOCATION: (32)..(33)
<223> OTHER INFORMATION: a, c, t, g, unknown or other

```
<220> FEATURE:
<221> NAME/KEY: modified_base
<222> LOCATION: (35)..(36)
<223> OTHER INFORMATION: a, c, t, g, unknown or other
<220> FEATURE:
<221> NAME/KEY: modified_base
<222> LOCATION: (41)..(42)
<223> OTHER INFORMATION: a, c, t, g, unknown or other
<220> FEATURE:
<221> NAME/KEY: modified_base
<222> LOCATION: (44)..(45)
<223> OTHER INFORMATION: a, c, t, g, unknown or other
<220> FEATURE:
<221> NAME/KEY: modified_base
<222> LOCATION: (47)..(48)
<223> OTHER INFORMATION: a, c, t, g, unknown or other
<220> FEATURE:
<221> NAME/KEY: modified_base
<222> LOCATION: (50)..(50)
<223> OTHER INFORMATION: a, c, t, g, unknown or other

<400> SEQUENCE: 106
ttgaccccag agatcgaagt asbnsnnssn snnanngtaa nngnnannwn bgcgtgcaca        60
atagtacata gc                                                           72

<210> SEQ ID NO 107
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 107
gagacggtga ccagagtacc ttgacccca                                         29

<210> SEQ ID NO 108
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 108
gagacggtga ccagagtacc ttgacccag daatcgaa                                38

<210> SEQ ID NO 109
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 109
gagacggtga ccagagtacc ttgacccag taatcgaagt a                            41

<210> SEQ ID NO 110
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 110
gagacggtga ccagagtacc ttgacccag agatcgaagt a                            41
```

```
<210> SEQ ID NO 111
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 111
ctaagcggcc gcgctcgaga cggtgaccag agtacc                                  36

<210> SEQ ID NO 112
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 112
atagctagcg cggatatcca gatgacccag agcc                                    34

<210> SEQ ID NO 113
<211> LENGTH: 55
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (29)..(29)
<223> OTHER INFORMATION: a, c, t, g, unknown or other

<400> SEQUENCE: 113
cccggtttct gctgatacca akycagrvng btaybgayay yctggctcgc gcggc             55

<210> SEQ ID NO 114
<211> LENGTH: 55
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 114
cccggtttct gctgatacca akycagcvag btaybgayay yctggctcgc gcggc             55

<210> SEQ ID NO 115
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 115
ataaattaac agtttcggcg ctttacccgg tttctgctga tacca                        45

<210> SEQ ID NO 116
<211> LENGTH: 59
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 116
```
aaagcgccga aactgttaat ttatrvkgcc agcavcckgs mgwctggcgt gccgtcgcg    59

<210> SEQ ID NO 117
<211> LENGTH: 55
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (17)..(18)
<223> OTHER INFORMATION: a, c, t, g, unknown or other
<220> FEATURE:
<221> NAME/KEY: modified_base
<222> LOCATION: (23)..(24)
<223> OTHER INFORMATION: a, c, t, g, unknown or other
<220> FEATURE:
<221> NAME/KEY: modified_base
<222> LOCATION: (29)..(30)
<223> OTHER INFORMATION: a, c, t, g, unknown or other
<220> FEATURE:
<221> NAME/KEY: modified_base
<222> LOCATION: (32)..(33)
<223> OTHER INFORMATION: a, c, t, g, unknown or other

<400> SEQUENCE: 117
gccctggccg aaggtsnntg gsnnvybsnn snnttgctgg caatagtagg tggcg    55

<210> SEQ ID NO 118
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 118
tcatagcggc cgcgcgtttg atctccactt tggtgccctg gccgaaggt    49

<210> SEQ ID NO 119
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 119
atagctagcg cgagctacga actgacccag c    31

<210> SEQ ID NO 120
<211> LENGTH: 67
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (23)..(23)
<223> OTHER INFORMATION: a, c, t, g, unknown or other

<400> SEQUENCE: 120
ccggtttctg ctgataccar ydnrcrkast dsbymssrak kbyrtygccr cygcaggtga    60
tacgcgc    67

<210> SEQ ID NO 121

```
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 121
gtaaatcacc agcaccggtg cctgacccgg tttctgctga tacca              45

<210> SEQ ID NO 122
<211> LENGTH: 48
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (26)..(26)
<223> OTHER INFORMATION: a, c, t, g, unknown or other
<220> FEATURE:
<221> NAME/KEY: modified_base
<222> LOCATION: (32)..(32)
<223> OTHER INFORMATION: a, c, t, g, unknown or other

<400> SEQUENCE: 122
caccggtgct ggtgatttac vrsranavyr ancgcccgtc tggcatcc           48

<210> SEQ ID NO 123
<211> LENGTH: 63
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (19)..(20)
<223> OTHER INFORMATION: a, c, t, g, unknown or other
<220> FEATURE:
<221> NAME/KEY: modified_base
<222> LOCATION: (24)..(24)
<223> OTHER INFORMATION: a, c, t, g, unknown or other
<220> FEATURE:
<221> NAME/KEY: modified_base
<222> LOCATION: (30)..(30)
<223> OTHER INFORMATION: a, c, t, g, unknown or other
<220> FEATURE:
<221> NAME/KEY: modified_base
<222> LOCATION: (33)..(33)
<223> OTHER INFORMATION: a, c, t, g, unknown or other

<400> SEQUENCE: 123
gtgccaccgc caaacacsnn rkrnkyrsyn synbtgtccs hyrmctggca gtaatagtcc    60
gcc                                                                 63

<210> SEQ ID NO 124
<211> LENGTH: 57
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (19)..(21)
<223> OTHER INFORMATION: a, c, t, g, unknown or other

<400> SEQUENCE: 124
gtgccaccgc caaacacsnn nsyrbyrbtg tcccayrmct ggcagtaata gtccgcc      57
```

<210> SEQ ID NO 125
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 125
tcatagcggc cgcgcccagc acggtcagtt tggtgccacc gccaaacac          49

<210> SEQ ID NO 126
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 126
ccagccatgg ccgatatcca gatgaccca                                29

<210> SEQ ID NO 127
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 127
cgtacgtttg atctccactt tggtgc                                   26

<210> SEQ ID NO 128
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 128
ccagccatgg ccagctacga actgacccag cc                            32

<210> SEQ ID NO 129
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 129
ggtcagtttg gtgccaccgc                                          20

<210> SEQ ID NO 130
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 130
ccagccatgg ccgaggtg                                            18

<210> SEQ ID NO 131
<211> LENGTH: 53
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 131
tcggacccaa ttcatccagt agtygyysah gkwsahtcca gaggctgcac agg          53

<210> SEQ ID NO 132
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 132
tactggatga attgggtccg                                                20

<210> SEQ ID NO 133
<211> LENGTH: 59
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 133
cacagagccc acatagtatt tctcgkhgcc gyyttggkhs ahtgcggcca cccactcca    59

<210> SEQ ID NO 134
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 134
gagaaatact atgtgggctc tgtg                                           24

<210> SEQ ID NO 135
<211> LENGTH: 59
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 135
cgaagtacca gtagtgtatg taataatcgc taatgavatc gtaatagtct ctcacacag    59

<210> SEQ ID NO 136
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 136

Gly Gly Gly Gly Ser Gly Gly Gly Gly Ser Gly Gly Gly Gly Ser
1               5                   10                  15

```
<210> SEQ ID NO 137
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 137
ggtggaggcg gttctggcgg aggtgggagc ggaggcggag gttca                45
```

ANTI-HUMAN IL-17 MONOCLONAL ANTIBODIES AND USE THEREOF

RELATED APPLICATIONS

This application is a 35 U.S.C. § 371 filing of International Application No. PCT/CN2016/074805, filed Feb. 29, 2016, which claims priority to Chinese Patent Application No. 201510097117.0, filed Mar. 5, 2015, each of which is incorporated herein by reference in its entirety.

SEQUENCE LISTING

The instant application contains a Sequence Listing which has been submitted electronically in ASCII format and is hereby incorporated by reference in its entirety. Said ASCII copy, created on Mar. 31, 2017, is named 589444_BBB9-001US_SL.txt and is 72,896 bytes in size.

TECHNICAL FIELD

The present invention generally relates to the field of genetic engineered antibody pharmaceuticals, and in particular, to an anti-human IL-17 monoclonal antibody and use thereof. A new human anti-human IL-17 monoclonal antibody, and the use of subject antibody in treating IL-17-meditated diseases are provided in the present invention.

BACKGROUND ART

Currently, the interleukin 17 (IL-17) family includes six cytokines, namely, IL-17A, IL-17B, IL-17C, IL-17D, IL-17E and IL-17F. The members of the IL-17 family do not share sequence similarity with any other known cytokines, and also share relatively low sequence similarity among themselves (Gaffen S L, Nat. Rev. Immunol. 2009 August; 9(8):556-67). Function of the IL-17 family members is mainly involved in the modulation of the immune response.

IL-17A, a homodimer glycoprotein of 20-30 kD, is mainly produced by activated CD4$^+$T cells, and acts as a pro-inflammatory cytokine. IL-17 is secreted by activated T cells at an inflammatory site, not during the systemic circulation. IL17 has many biological properties, including up-regulating adhesion molecules, and inducing the production of numerous inflammatory cytokines and chemokines in various cell types, including synovial cells, cartilage cells, fibroblasts, endothelial cells, epithelial cells, keratinocytes and macrophages. In addition, IL-17 induces the aggregation of neutrophilic granulocytes at an inflammation site by inducing the release of chemokines, stimulates the production of prostaglandins and metalloproteases, and inhibits the synthesis of proteoglycans. Moreover, IL-17 plays a critical role in the maturation of hemopoietic progenitor cells. IL-17 is involved in the signal transduction in various organs and tissues, including lung, articular cartilage, bone, brain, hemopoietic cells, kidneys, skin and intestines. Therefore, the immune reaction mediated by IL-17A/Th17 is systemic, and leads to an inflammatory reaction mainly expressed as neutrophilic granulocyte infiltration.

As demonstrated by extensive studies, the increase in IL-17 is involved in various diseases, including airway inflammation, rheumatoid arthritis (RA), osteoarthritis, bone erosion, inflammatory bowel disease (IBD), allograft rejection, psoriasis, some types of cancer, angiogenesis, atherosclerosis and multiple sclerosis (MS) (Witkowski et al., Cell. Mol. Life Sci. 61:567-579, 2004). Additionally, IL-17 plays a role in the degradation of collagen matrix, inflammation and joint injury, independent of IL-lb. Also, IL-17 and TNF-α synergistically increase inflammation. As confirmed by further studies, by blocking the in vivo biological activity of IL-17 with an antibody specifically binding to IL-17 or a soluble IL17 receptor, inflammation and bone erosion in various animal arthritis models are effectively reduced. Therefore, IL-17 becomes a new therapeutic target for RA and other autoimmune diseases. Moreover, since IL17 is mainly present in an inflammatory site, a medicament targeting IL17 may potentially have higher safety than medicaments targeting other pro-inflammatory cytokines in systemic circulation (e.g. TNF).

Currently, European Union and the FDA in the US have approved Cosentyx from Novartis Pharma AG for treating adult patients suffering from moderate-to-severe plaque psoriasis. The active ingredient of Cosentyxus is secukinumab, which is a monoclonal antibody against IL-17. Nevertheless, there is still a need in the art in more improved anti-IL-17 antibodies suitable for treatment of a patient.

SUMMARY OF INVENTIONS

In an aspect, there is provided in the present application is a monoclonal antibody that specifically binds to human IL-17A, comprising a heavy chain variable region comprising HCDR1, HCDR2 and HCDR3, wherein HCDR1 has the sequence $GX_1X_2X_3X_4X_5Y$, HCDR2 has the sequence $NQDGX_6E$ (SEQ ID NO: 35), and HCDR3 has the sequence $DYYDX_7ISDYYIHYWYFDL$ (SEQ ID NO: 36); wherein the sequence $X_1X_2X_3X_4X_5$ is FTIDN (SEQ ID NO: 37), MSMSD (SEQ ID NO: 38) or ITMDD (SEQ ID NO: 39), $X_6$ is N or D, $X_7$ is V or L; and wherein the HCDRs are defined according to Chothia.

In some embodiments, the heavy chain variable region of the antibody has an amino acid sequence as set forth in SEQ ID NO: 24, 25 or 26.

In an aspect, there is provided in the present application is a monoclonal antibody that specifically binds to human IL-17A, comprising a light chain variable region comprising LCDR1, LCDR2 and LCDR3, wherein LCDR1 has the sequence RASQNVHNRLT (SEQ ID NO: 40), LCDR2 has the sequence GASNLES (SEQ ID NO: 41), and LCDR3 has the sequence QQYNGSPTT (SEQ ID NO: 42); and wherein the LCDRs are defined according to Chothia.

In some embodiments, the light chain variable region of the antibody has an amino acid sequence as set forth in SEQ ID NO: 21.

In an aspect, there is provided in the present application is a monoclonal antibody that specifically binds to human IL-17A, comprising a heavy chain variable region comprising HCDR1, HCDR2 and HCDR3, and a light chain variable region comprising LCDR1, LCDR2 and LCDR3, wherein HCDR1 has the sequence $GX_1X_2X_3X_4X_5Y$, HCDR2 has the sequence $NQDGX_6E$ (SEQ ID NO: 35), HCDR3 has the sequence $DYYDX_7ISDYYIHYWYFDL$ (SEQ ID NO: 36), LCDR1 has the sequence RASQNVHNRLT (SEQ ID NO: 40), LCDR2 has the sequence GASNLES (SEQ ID NO: 41), and LCDR3 has the sequence QQYNGSPTT (SEQ ID NO: 42); wherein the sequence $X_1X_2X_3X_4X_5$ is FTIDN (SEQ ID NO: 37), MSMSD (SEQ ID NO: 38) or ITMDD (SEQ ID NO: 39), $X_6$ is N or D, and $X_7$ is V or L; and wherein the HCDRs and LCDRs are defined according to Chothia.

In some embodiments, the heavy chain variable region of the antibody has a sequence as set forth in SEQ ID NO: 24, and the light chain variable region has a sequence as set forth in SEQ ID NO:21; or the heavy chain variable region has a sequence as set forth in SEQ ID NO: 25, and the light chain variable region has a sequence as set forth in SEQ ID NO:21; or the heavy chain variable region has a sequence as set forth in SEQ ID NO: 26, and the light chain variable region has a sequence as set forth in SEQ ID NO:21.

In some embodiments in the above three aspects, the antibody is an intact antibody, a substantively intact antibody, a Fab fragment, a F(ab')$_2$ fragment or a single-chain Fv fragment.

In some embodiments in the above three aspects, the antibody is a fully human antibody.

In some embodiments in the above three aspects, the antibody further comprises a heavy chain constant region selected from the group consisting of IgG1 and IgG4 subtypes, and/or a light chain constant region selected from the group consisting of kappa and lambda subtypes.

In some embodiments in the above three aspects, the monoclonal antibody is capable of inhibiting the activity of 2 nM human IL-17A by 50% at a concentration less than 1 nM, wherein the activity inhibition is measured by determining human IL-17A-induced IL-6 production in human dermal fibroblasts (HDFa).

In an aspect, there is provided in the present application is a pharmaceutical composition comprising a monoclonal antibody in any one of the above aspects.

In an aspect, there is provided in the present application is use of a monoclonal antibody in any one of the above aspects in treating a human IL-17A-mediated disease.

In some embodiments, the disease is an autoimmune disease.

In some embodiments, the disease is psoriasis, rheumatoid arthritis or ankylosing spondylitis.

In an aspect, there is provided in the present application is use of a monoclonal antibody in any one of the above aspects in the manufacture of a medicament for treating a human IL-17A-mediated disease.

In some embodiments, the disease is an autoimmune disease.

In some embodiments, the disease is psoriasis, rheumatoid arthritis or ankylosing spondylitis.

In an aspect, there is provided in the present application is a method for treating a human IL-17A-mediated disease, comprising administering a monoclonal antibody in any one of the above aspects to a subject in need thereof.

In some embodiments, the disease is an autoimmune disease.

In some embodiments, the disease is psoriasis, rheumatoid arthritis or ankylosing spondylitis.

DETAILED DESCRIPTION OF INVENTIONS

Figure 1:
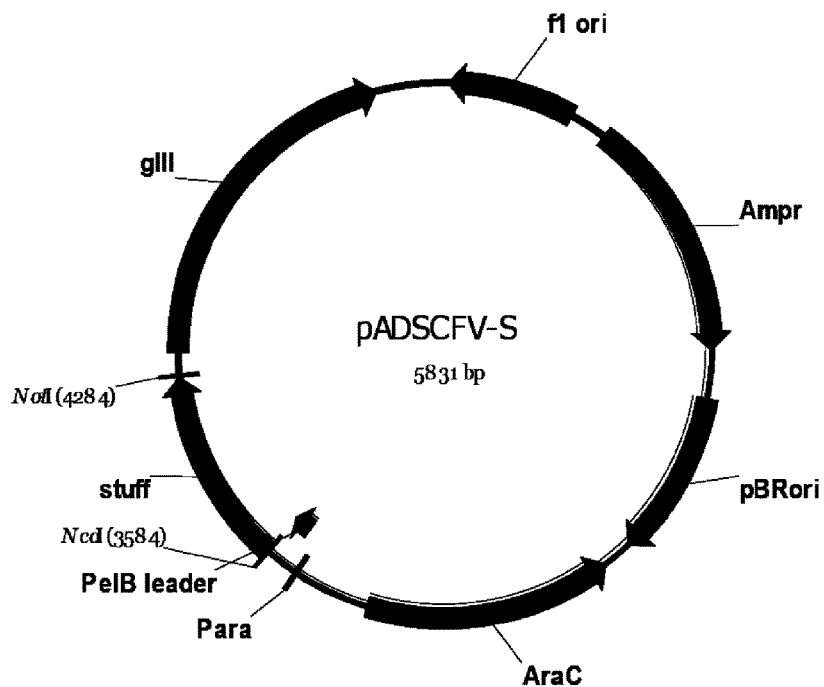
FIG. 1 shows a structural diagram of a novel phage display vector pADSCFV-S (Para: arabinose promoter, PelB leader: PelB signal peptide gene, NcoI: NcoI restriction site, Stuff: 750 bp stuff sequence, NotI: NotI restriction site, gIII: gIII gene of M13 phage, flori: replication origin of M13 phage, Ampr: ampicillin resistance gene, pBRori: replication origin of pBR322, AraC: AraC gene).

Various inventions in the present application are partially based on construction of human phage antibody library. The inventors have screened human anti-IL-17 monoclonal antibodies with desired properties from the constructed antibody library.

In various aspects of the present application, there is provided a novel anti-human IL-17 monoclonal antibody or an antigen-binding fragment thereof, a polynucleotide encoding the monoclonal antibody or the antigen-binding fragment, a vector comprising the polynucleotide, a host cell comprising the polynucleotide or the vector, a method for preparing and purifying the antibody, and medical use of the antibody or the antigen-binding fragment. Based on the sequences of viable regions of the antibody of the present application, an intact antibody molecule can be formulated as a medicament for clinically treating an IL-17-mediated autoimmune disease, including but not limited to psoriasis, rheumatoid arthritis and ankylosing spondylitis.

Unless otherwise specified, all technical and scientific terms used herein have the same meaning as those understood by an ordinary person skilled in the relevant art.

As used herein, the term "polypeptide" refers to a polymer constituted by amino acid residues linked via a peptide bond. The term "protein" usually refers to a relatively large polypeptide. The term "peptide" usually refers to a relatively small polypeptide (e.g., containing at most 100, 80, 60, 50, 30 or 20 amino acid residues).

As used herein, the term "antibody" refers to an immunoglobulin molecule that specifically binds to a target via at least one antigen recognition epitope in the variable region of the immunoglobulin molecule. The examples of the target include but not limited to a carbohydrate, a polynucleotide, a lipid, a polypeptide. As used herein, the term "antibody" includes not only an intact (full-length) antibody, but also an antigen-binding fragment (e.g., Fab, Fab', F(ab')$_2$, Fv), a variant, a fusion protein comprising an antibody portion, a humanized antibody, a chimeric antibody, a diabody, a linear antibody, a single-strand antibody, a multi-specific antibody thereof (e.g., a bi-specific antibody), and any other modified versions of an immunoglobulin molecule comprising the antigen recognition site exhibiting desired specificity, including a glycosylated variant of an antibody, a variant of an antibody with a modified amino acid sequence, and a covalently modified antibody.

Generally, an intact or full-length antibody comprises two heavy chains and two light chains. Each heavy chain comprises a heavy chain variable region (VH) and a first, second and third constant region (CH1, CH2 and CH3). Each light chain comprises a light chain variable region (VL) and a constant region (CL). A full-length antibody may be an antibody of any classes, e.g., IgD, IgE, IgG, IgA or IgM (or a subclass of the above). However, the antibody of the present application does not necessarily belong to any specific class. Based on the amino acid sequence of the constant domain of the heavy chain of an antibody, an immunoglobulin can be divided into different classes. Generally, there are five classes of immunoglobulins, i.e., IgA, IgD, IgE, IgG and IgM. Some of these classes can be further divided into several subclasses (isoforms), e.g., IgG1, IgG2, IgG3, IgG4, IgA1 and IgA2. Constant domains of heavy chains of different classes of immunoglobulins are termed as α, δ, ε, γ and μ. The structures of subunits and the three-dimensional structures of various classes of immunoglobulins are well known in the art.

As used herein, the term "antigen-binding fragment" refers to a portion or region of an intact antibody molecule that is responsible for binding to an antigen. An antigen-binding domain may comprise a heavy chain variable region (VH), a light chain variable region (VL) or both. Each of VH and VL generally comprises three complementary determining regions, i.e., CDR1, CDR2 and CDR3.

Examples of an antigen-binding fragment include but not limited to, (1) a Fab fragment, which may be a monovalent fragment comprising a VL-CL chain and a VH-CH1 chain; (2) a F(ab')$_2$ fragment, which may be a bivalent fragment comprising two Fab fragments which are linked by a disulfide bridge in the hinge region (i.e. a dimer of Fab); (3) a Fv fragment comprising a VL domain and a VH domain from a single arm of an antibody; (4) a single-chain Fv (scFv), which may be a single polypeptide chain comprising a VH domain and a VL domain linked by a peptide linker; and 5) (scFv)$_2$, which may comprise two VH domains linked by a peptide linker and two VL domains which are conjugated to the two VH domains via a disulfide bridge.

As used herein, the term "specifically bind to" refer to a non-random binding reaction between two molecules, e.g., binding of an antibody to an antigen epitope.

The nucleic acid sequences provided herein involve use of degenerate bases in addition to the conventional A, T, C and G The meaning of a degenerate base is the same as that commonly understood by a person skilled in the art. For example, R refers to A or G, Y refers to C or T, M refers to A or C, K refers to G or T, S refers to C or G W refers to A or T, H refers to A or C or T, B refers to C or G or T, V refers to A or C or G, D refers to A or G or T, and N refers to A or C or G or T.

In an aspect, there is provided in the present application is a monoclonal antibody that specifically binds to human IL-17A, comprising a heavy chain variable region comprising HCDR1, HCDR2 and HCDR3, wherein HCDR1 has the sequence GX$_1$X$_2$X$_3$X$_4$X$_5$Y, HCDR2 has the sequence NQDGX$_6$E (SEQ ID NO: 35), and HCDR3 has the sequence DYYDX$_7$ISDYYIHYWYFDL (SEQ ID NO: 36); wherein the sequence X$_1$X$_2$X$_3$X$_4$X$_5$ is FTIDN (SEQ ID NO: 37), MSMSD (SEQ ID NO: 38) or ITMDD (SEQ ID NO: 39), X$_6$ is N or D, X$_7$ is V or L; and wherein the HCDRs are defined according to Chothia.

In some embodiments, the heavy chain variable region of the antibody has an amino acid sequence as set forth in SEQ ID NO: 24, 25 or 26.

In an aspect, there is provided in the present application is a monoclonal antibody that specifically binds to human IL-17A, comprising a light chain variable region comprising LCDR1, LCDR2 and LCDR3, wherein LCDR1 has the sequence RASQNVHNRLT (SEQ ID NO: 40), LCDR2 has the sequence GASNLES (SEQ ID NO: 41), and LCDR3 has the sequence QQYNGSPTT (SEQ ID NO: 42); and wherein the LCDRs are defined according to Chothia.

In some embodiments, the light chain variable region of the antibody has an amino acid sequence as set forth in SEQ ID NO: 21.

In an aspect, there is provided in the present application is a monoclonal antibody that specifically binds to human IL-17A, comprising a heavy chain variable region comprising HCDR1, HCDR2 and HCDR3, and a light chain variable region comprising LCDR1, LCDR2 and LCDR3, wherein HCDR1 has the sequence GX$_1$X$_2$X$_3$X$_4$X$_5$Y, HCDR2 has the sequence NQDGX$_6$E (SEQ ID NO: 35), HCDR3 has the sequence DYYDX$_7$ISDYYIHYWYFDL (SEQ ID NO: 36), LCDR1 has the sequence RASQNVHNRLT (SEQ ID NO: 40), LCDR2 has the sequence GASNLES (SEQ ID NO: 41), and LCDR3 has the sequence QQYNGSPTT (SEQ ID NO: 42); wherein the sequence X$_1$X$_2$X$_3$X$_4$X$_5$ is FTIDN (SEQ ID NO: 37), MSMSD (SEQ ID NO: 38) or ITMDD (SEQ ID NO: 39), X$_6$ is N or D, and X$_7$ is V or L; and wherein the HCDRs and LCDRs are defined according to Chothia.

In some embodiments, the heavy chain variable region of the antibody has a sequence as set forth in SEQ ID NO: 24, and the light chain variable region has a sequence as set forth in SEQ ID NO:21; or the heavy chain variable region has a sequence as set forth in SEQ ID NO: 25, and the light chain variable region has a sequence as set forth in SEQ ID NO:21; or the heavy chain variable region has a sequence as set forth in SEQ ID NO: 26, and the light chain variable region has a sequence as set forth in SEQ ID NO:21.

In some embodiments in the above three aspects, the antibody is an intact antibody, a substantively intact antibody, a Fab fragment, a F(ab')$_2$ fragment or a single-chain Fv fragment.

In some embodiments in the above three aspects, the antibody is a fully human antibody.

In some embodiments in the above three aspects, the antibody further comprises a heavy chain constant region selected from the group consisting of IgG1 and IgG4 subtypes, and/or a light chain constant region selected from the group consisting of kappa and lambda subtypes.

In some embodiments in the above three aspects, the monoclonal antibody is capable of inhibiting the activity of 2 nM human IL-17A by 50% at a concentration less than 1 nM, wherein the activity inhibition is measured by determining human IL-17A-induced IL-6 production in human dermal fibroblasts (HDFa).

In some embodiments in the above three aspects, the antibody is a fully human monoclonal antibody, and reduces, antagonizes or eliminates at least one in vitro or in vivo biological activity involving IL-17 or a portion thereof.

In some embodiments in the above three aspects, the antibody is characterized by high binding affinity to human IL-17.

In some embodiments in the above three aspects, the antibody is characterized in that it can specifically bind to human IL-17, *Macaca mulatta* IL-17 and *Macaca fascicularis* IL-17 at a level higher than background, but not *Mus musculus* IL-17.

In some embodiments in the above three aspects, the antibody comprises a variable region and a constant region, wherein the heavy chain constant region may be of IgG1 subtype (SEQ ID NO: 29) or IgG4 subtype (SEQ ID NO: 30), and the light chain constant region may be of kappa subtype (SEQ ID NO: 31) or lambda subtype (SEQ ID NO: 32).

In another aspect, there is provided in the present application is a polynucleotide encoding a monoclonal antibody or an antigen-binding fragment thereof in the above aspects, a vector comprising the polynucleotide, and a host cell transfected with the vector. In some embodiments, the host cell is a CHO cell or a HEK293 cell.

In an aspect, there is provided in the present application is a pharmaceutical composition comprising a monoclonal antibody in any one of the above aspects.

In some embodiments, the pharmaceutical composition further comprises a pharmaceutically acceptable carrier, excipient and/or diluent.

In some embodiments, the pharmaceutical composition comprises a therapeutically effective amount of the monoclonal antibody.

In an aspect, there is provided in the present application is use of a monoclonal antibody in any one of the above aspects in treating a human IL-17A-mediated disease.

In some embodiments, the disease is an autoimmune disease.

In some embodiments, the disease is psoriasis, rheumatoid arthritis or ankylosing spondylitis.

In an aspect, there is provided in the present application is use of a monoclonal antibody in any one of the above aspects in the manufacture of a medicament for treating a human IL-17A-mediated disease.

In some embodiments, the disease is an autoimmune disease.

In some embodiments, the disease is psoriasis, rheumatoid arthritis or ankylosing spondylitis.

In an aspect, there is provided in the present application is a method for treating a human IL-17A-mediated disease, comprising administering a monoclonal antibody in any one of the above aspects to a subject in need thereof.

In some embodiments, the disease is an autoimmune disease.

In some embodiments, the disease is psoriasis, rheumatoid arthritis or ankylosing spondylitis.

In some embodiments, the pharmaceutical activity of an antibody of the present application can be tested by a standard assay in the art, e.g., see, Hwang S Y, Kim J Y, Kim K W, Park M K, Moon Y, Kim W U, Kim H Y: IL-17 induces production of IL-6 and IL-8 in rheumatoid arthritis synovial fibroblasts via NF-kappaB- and PI3-kinase/Akt-dependent pathways. Arthritis research & therapy 2004, 6(2):R120-128. Briefly, in the presence of an antibody of the present application at various concentrations, the recombinant IL-17 is used to stimulate human dermal fibroblasts (HDFa cells). After stimulated for 24 h, supernatant is obtained and detected for IL-6 by an ELISA assay. When the above test is carried out, an antibody of the present application preferably has an $IC_{50}$ value of about 0.22 nM or less, more preferably about 0.12 nM or less, and even more preferably about 0.07 nM or less in respect of inhibition of production of IL-6 as defined above.

In some embodiments, the stability of an antibody of the present application in human serum can be tested by a standard assay in the art. Briefly, a monoclonal antibody sample sterilized by filtration is diluted into 200 µl of sterilized normal human serum mixture or PBS to a final concentration of 30 µg/ml, respectively, mixed and placed in a water bath at 37° C. for 8 days (192 h). Next, monoclonal antibodies in the serum sample, monoclonal antibodies in the PBS sample and monoclonal antibodies from a cryopreserved sample are assessed for their binding to human IL17 by an ELISA assay. The change in binding capabilities of the monoclonal antibodies in different samples to IL17 is compared. When the above test is carried out, an antibody of the present application preferably retains about 87%, more preferably about 91%, and even more preferably about 97% of IL17 binding capability.

In some embodiments, the pharmacokinetics of an antibody of the present application in mice can be assessed by a standard assay in the art. Briefly, a monoclonal antibody sample is formulated in a PBS buffer (pH7.0) at a concentration of 0.5 mg/ml, and administered to mice at a dosage of 5 mg/kg with a single injection into tail vein. Each group contains eight BALB/c mice with four male and four female. Blood samples are then taken by intra-orbital sampling at 4, 24, 48, 96, 168, 240 and 336 hours after injection, and stored at −70° C. After all samples are obtained, the concentrations of the monoclonal antibody in the samples are quantitatively determined. The quantitation of plasma concentration of a drug is carried out based on a quantitative ELISA assay with coated IL17. According to the first order reaction model, the natural logarithm of the antibody concentration (ln C) is plotted with respect to time (t), yielding a slope constant k. Then, the half-life of the anti-IL17 monoclonal antibody in mice (t1/2) is calculated according to the formula t1/2=0.693/k. When the above test is carried out, an antibody of the present application preferably has a half-life (t1/2) in mice of about 6.7 h, more preferably about 7.4 h, and even more preferably about 8.5 h.

In an aspect, there is provided in the present application is an isolated nucleic acid molecule encoding an antibody of the present application or a light chain or a heavy chain thereof, a vector comprising the nucleic acid molecule, a host cell comprising the vector, and a method for producing the antibody. In some embodiments, the nucleic acid molecule is operatively linked to a regulatory sequence, which can be recognized by a host cell transformed with the vector. In some embodiments, the method for producing the antibody comprises culturing the host cell such that the nucleic acid is expressed. In some embodiments, the method for producing the antibody further comprises recovering the antibody from the culture medium in which the host cell is cultured.

In an aspect, there is provided in the present application is *Mus musculus* IL-17 (SEQ ID NO:9), *Macaca mulatta* IL-17 (SEQ ID NO:10) or *Macaca fascicularis* IL-17 (SEQ ID NO:11), an isolated nucleic acid molecule encoding any one of them, a vector comprising the nucleic acid molecule, a host cell comprising the vector, a method for producing the *Mus musculus* IL-17, *Macaca mulatta* IL-17 or *Macaca fascicularis* IL-17.

EXAMPLES

The following examples are provided only for the purpose of further illustrating the inventions of the present application, but should not be construed as any limitation to the inventions.

Example 1: Construction of High-Quality Phage Display Antibody Library

Antibody library technique is an important method for preparing human monoclonal antibodies. Currently, antibody library technique based on phage display had been well-established, and successfully applied to preparation of human monoclonal antibodies. This example demonstrates the strategy and methodology for constructing a phage display antibody library using many genetic engineering techniques.

1.1 Preparation of Genes of Antibody Heavy Chain and Light Chain Variable Region (VH and VL)

In order to construct a human antibody library, genes of heavy chain variable regions (VH) and light chain variable regions (VL) of human antibodies must be acquired first. Genes of antibody variable regions may be derived from lymphocytes in peripheral blood from healthy subjects or fully synthesized.

1.1.1 Preparation of Genes of Natural Human Antibody Variable Regions

Blood was taken from 19 healthy volunteers (50 ml for each). Then, lymphocytes were isolated using a lymphocyte isolation solution (MP Biomedicals Inc., Cat#:0850494). RNA was prepared using a Total RNA extraction kit from Omega Inc. (Cat#:R6834-01). The cDNA was prepared using a reverse transcription kit from TransGen Biotech Inc. (Cat#:AT301-03). Finally, the primer sets shown in the Table 1 below were used in a PCR reaction to amplify heavy chain variable region genes (VH) and light chain variable region genes (VL, including Vk and Vl) of antibodies, respectively. Amplified PCR products (VH,VK or Vl) were purified and recovered using standard agarose gel electrophoresis, and stored at −20° C. for further use.

TABLE 1

Primers for amplifying natural human antibody heavy chain and light chain genes

| primer | | primer sequence | SEQ ID NO: |
|---|---|---|---|
| VH forward primer | VHF1 | CAGRTGCAGCTGGTGCARTCTGG | 43 |
| | VHF2 | SAGGTCCAGCTGGTRCAGTCTGG | 44 |
| | VHF3 | CAGRTCACCTTGAAGGAGTCTGG | 45 |
| | VHF4 | SAGGTGCAGCTGGTGGAGTCTGG | 46 |
| | VHF5 | GAGGTGCAGCTGGTGGAGWCYGG | 47 |
| | VHF6 | CAGGTGCAGCTACAGCAGTGGGG | 48 |
| | VHF7 | CAGSTGCAGCTGCAGGAGTCSGG | 49 |
| | VHF8 | GARGTGCAGCTGGTGCAGTCTGG | 50 |
| | VHF9 | CAGGTACAGCTGCAGCAGTCAGG | 51 |
| VH reverse primer | VHR1 | TGAGGAGACGGTGACCAGGGTGCC | 52 |
| | VHR2 | TGAAGAGACGGTGACCATTGTCCC | 53 |
| | VHR3 | TGAGGAGACGGTGACCAGGGTTCC | 54 |
| | VHR4 | TGAGGAGACGGTGACCGTGGTCCC | 55 |
| VK forward primer | VKF1 | GACATCCAGWTGACCCAGTCTCC | 56 |
| | VKF2 | GATGTTGTGATGACTCAGTCTCC | 57 |
| | VKF3 | GAAATTGTGWTGACRCAGTCTCC | 58 |

TABLE 1 -continued

Primers for amplifying natural human antibody heavy chain and light chain genes

| primer | | primer sequence | SEQ ID NO: |
|---|---|---|---|
| | VKF4 | GATATTGTGATGACCCAGACTCC | 59 |
| | VKF5 | GAAACGACACTCACGCAGTCTCC | 60 |
| | VKF6 | GAAATTGTGCTGACTCAGTCTCC | 61 |
| VK reverse primer | VKR1 | ACGTTTGATCTCGAGCTTGGTCCCYTGGCCRAA | 62 |
| | VKR2 | ACGTTTGATCTCGAGTTTGGTCCCAGGGCCGAA | 63 |
| | VKR3 | ACGTTTGATCTCGAGCTTGGTCCCTCCGCCGAA | 64 |
| | VKR4 | ACGTTTAATCTCGAGTCGTGTCCCTTGGCCGAA | 65 |
| Vl forward primer | VlF1 | CAGTCTGTGYTGACKCAGCCRCC | 66 |
| | VlF2 | CARTCTGCCCTGACTCAGCCT | 67 |
| | VlF3 | TCCTATGWGCTGACTCAGCCA | 68 |
| | VlF4 | TCTTCTGAGCTGACTCAGGACCC | 69 |
| | VlF5 | CAGGCTGTGCTGACTCAGCCG | 70 |
| | VlF6 | AATTTTATGCTGACTCAGCCCCA | 71 |
| | VlF7 | CAGRCTGTGGTGACYCAGGAGCC | 72 |
| | VlF8 | CWGCCTGTGCTGACTCAGCC | 73 |
| Vl reverse primer | VlR1 | ACCTAGGACGGTGACCTTGGTCCC | 74 |
| | VlR2 | ACCTAGGACGGTCAGCTTGGTCCC | 75 |
| | VlR3 | ACCTAAAACGGTGAGCTGGGTCCC | 76 |

1.1.2 Preparation of Fully Synthesized Human Antibody Variable Region Genes The basic strategy of preparation of fully synthesized antibody genes involves using degenerate primers to introduce designed mutations into CDRs of a chosen antibody gene template. In order to construct a fully synthesized human antibody library, three human antibody heavy chain variable region templates (VH1;VH3 and VH5) and two human antibody light chain variable region templates (VK1 and Vl3) were chosen in this example to construct a fully synthesized human antibody library.

Five antibody variable region genes, i.e., VH1 (SEQ ID NO:1), VH3 (SEQ ID NO:2), VH5 (SEQ IDNO:3), VK1 (SEQ ID NO:4) and V13 (SEQ ID NO:5), were designed and synthesized by Ming Chen Zhi Yuan Inc. Primers as shown in Table 2 were designed and synthesized to introduce designed mutations into the CDR1, CDR2 and CDR3 of the five variable region genes, respectively. By using the conventional PCR technique and respective sets of degenerate primers containing the designed mutations, the designed mutations were introduced into corresponding CDRs. Then, by using 2-3 rounds of overlapping PCR, intact heavy chain variable region genes (VH1.VH3,VH5) or light chain variable region genes (VK1,VL3) were constructed. Finally, amplified PCR products of the variable region genes were recovered by agarose gel electrophoresis, and stored at −20° C. for further use.

TABLE 2

Primers for amplifying fully synthesized human antibody variable region genes.

| primer | primer | sequence | SEQ ID NO: |
|---|---|---|---|
| VH1 | CDR1 | PVH1-1: ACTAGCTAGCGCGCAGGTGCAGTTAGTGCAGAG | 77 |
| | | PVH1-2: GGTGCCTGACGCACCCARYKNATRKMATARYYRSTAAAGGTGCCGCCACTC | 78 |

TABLE 2 -continued

Primers for amplifying fully synthesized human antibody variable region genes.

| primer | | primer sequence | SEQ ID NO: |
|---|---|---|---|
| | CDR2 | PVH1-3: GCCCATCCATTCCAGGCCCTGTCCCGGTGCCTGACGCACCCA | 79 |
| | | PVH1-4: GGCCTGGAATGGATGGGCKGGATAANYCCGWWYTYYGGCRVY RCNAANTATGCGCAGAAATTCCAAGGC | 80 |
| | CDR3 | PVH1-5A: GTGCCCTGGCCCCAATAGTCSNNSNNSNNSNNSNNSNNSNNSN BACGGGCGCAATAATACACAG | 81 |
| | | PVH1-5B: GTGCCCTGGCCCCAATAGTCSRNSBNSYNSNNSNNSNNSNNSNN SNBSNBACGGGCGCAATAATACACAG | 82 |
| | | PVH1-5C: GTGCCCTGGCCCCAATAGTCGAASNNSNNSNNSNNRNNSNNRN NSNNSNNSNNSNBACGGGCGCAATAATACACAG | 83 |
| | | PVH1-6: TCATAGCGGCCGCAGATGACACAGTCACCAGGGTGCCCTGGCCC CAATAG | 84 |
| | | PVH1-7b: TCATAGCGGCCGCCGCGGTGCTGGTAGATTTGTC | 85 |
| VH3 | CDR1 | PVH3-1: ATAGCTAGCGCGGAAGTGCAATTGGTGGAAAGC | 86 |
| | | PVH3-2: GTGCCTGGCGCACCCARYKCATCSMGTARBYGCTAAAGGTGAA GCCGCTC | 87 |
| | | PVH3-2a: GTGCCTGGCGCACCCATGACATCSMGTAGCTGCTAAAGGTGAA GCC | 88 |
| | | PVH3-2B: GTGCCTGGCGCACCCAGTGCATCSMGTAGCTGCTAAAGGTGAA GCC | 89 |
| | CDR2 | PVH3-3: CACCCATTCCAGACCTTTACCCGGTGCCTGGCGCACCCA | 90 |
| | | PVH3-4: GGTAAAGGTCTGGAATGGGTGKCMKKYATTARNKVYRRYGGCR RYWMYAMRTACTATGCGGATAGCGTGAAAG | 91 |
| | CDR3 | PVH3-5a: TGCCCTGACCCCAGTAATCMADSNNSNNRNNSNNSNNRNNSBB YYTTGCGCAATAATACACCGC | 92 |
| | | PVH3-5B: TGCCCTGACCCCAGTAATCMADSSNSSNSSNSSNSSNSSNSS NNYYYYTTGCGCAATAATACACCGC | 93 |
| | | PVH3-5C: TGCCCTGACCCCAGTAATCMADSNNRYMSNNSNNSNNSNNSNN SNNRDNRNNNYYYBTTGCGCAATAATACACCGC | 94 |
| | | PVH3-6: TCATAGCGGCCGCGCTCGACACGGTCACCAGAGTGCCCTGACCC CAGTAATC | 95 |
| VH5 | CDR1 | PVH5-1: CAGCCATGGCCGAAGTTC | 96 |
| | | PVH5-2: CYGATCCAGTAGBTGGTGAAWSTATAACCAGAGCCTTTGCAG | 97 |
| | | PVH5-4: CTGGCATCTGGCGAACCCAACYGATCCAGTAGBTGGTGAA | 98 |
| | | PVH5-6: TACCCATCCATTCCAGACCTTTGCCTGGCATCTGGCGAACC | 99 |
| | CDR2 | PVH5-3: ACCCARGTGACAGCDACACCAVWTATTCTCCAAGCTTCCAGGG | 100 |
| | | PVH5-5: GGTCTGGAATGGATGGGTAKAATTDACCCARGTGACAGCDACAC | 101 |
| | | PVH5-8: CTAAGCGGCCGCGCGTGCACAATAGTACATAGC | 102 |
| | CDR3 | PVH5-10a: CCAGAGTACCTTGACCCCAADRGKMGWRSNNSNNSNNSNNSNNS NGHSGCGTGCACAATAGTACATAGC | 103 |
| | | PVH5-10b: TTGACCCCAGDAATCGAAGDNAHNSNNAVCSNNSNNTNSSNB GCGTGCACAATAGTACATAGC | 104 |
| | | PVH5-10c: TTGACCCCAGTAATCGAAGTASNNSNNABHWNBANNGNNANN SNNGCGTGCACAATAGTACATAGC | 105 |
| | | PVH5-10d: TTGACCCCAGAGATCGAAGTASBNSNNSSNNANNGTAANN GNNANNWNBGCGTGCACAATAGTACATAGC | 106 |

TABLE 2 -continued

Primers for amplifying fully synthesized human antibody variable region genes.

| primer | | primer sequence | SEQ ID NO: |
|---|---|---|---|
| | | PVH5-12a: GAGACGGTGACCAGAGTACCTTGACCCCA | 107 |
| | | PVH5-12b: GAGACGGTGACCAGAGTACCTTGACCCCAGDAATCGAA | 108 |
| | | PVH5-12c: GAGACGGTGACCAGAGTACCTTGACCCCAGTAATCGAAGTA | 109 |
| | | PVH5-12d: GAGACGGTGACCAGAGTACCTTGACCCCAGAGATCGAAGTA | 110 |
| | | PVH5-14: CTAAGCGGCCGCGCTCGAGACGGTGACCAGAGTACC | 111 |
| VK1 | CDR1 | PVK1-1: ATAGCTAGCGCGGATATCCAGATGACCCAGAGCC | 112 |
| | | PVK1-2a: CCCGGTTTCTGCTGATACCAAKYCAGRVNGBTAYBGAYAYYCTGGCTCGCGCGGC | 113 |
| | | PVK1-2b: CCCGGTTTCTGCTGATACCAAKYCAGCVAGBTAYBGAYAYYCTGGCTCGCGCGGC | 114 |
| | CDR2 | PVK1-3: ATAAATTAACAGTTTCGGCGCTTTACCCGGTTTCTGCTGATACCA | 115 |
| | | PVK1-4: AAAGCGCCGAAACTGTTAATTTATRVKGCCAGCAVCCKGSMGWCTGGCGTGCCGTCGCG | 116 |
| | CDR3 | PVK1-5: GCCCTGGCCGAAGGTSNNTGGSNNVYBSNNSNNTTGCTGGCAATAGTAGGTGGCG | 117 |
| | | PVK1-6: TCATAGCGGCCGCGCGTTTGATCTCCACTTTGGTGCCCTGGCCGAAGGT | 118 |
| VL3 | CDR1 | PVL3-1: ataGCTAGCGCGAGCTACGAACTGACCCAGC | 119 |
| | | PVL3-2: CCGGTTTCTGCTGATACCARYDNRCRKASTDSBYMSSRAKKBYRTYGCCRCYGCAGGTGATACGCGC | 120 |
| | CDR2 | PVL3-3: GTAAATCACCAGCACCGGTGCCTGACCCGGTTTCTGCTGATACCA | 121 |
| | | PVL3-4: CACCGGTGCTGGTGATTTACVRSRANAVYRANCGCCCGTCTGGCATCC | 122 |
| | CDR3 | PVL3-5a: GTGCCACCGCCAAACACSNNRKRNKYRSYNSYNBTGTCCSHYRMCTGGCAGTAATAGTCCGCC | 123 |
| | | PVL3-5b: GTGCCACCGCCAAACACSNNNSYRBYRBTGTCCCAYRMCTGGCAGTAATAGTCCGCC | 124 |
| | | PVL3-6: TCATAGCGGCCGCGCCCAGCACGGTCAGTTTGGTGCCACCGCCAACAC | 125 |

1.2 Construction of Single-Chain Antibody (Single Chain Fv, ScFv) Genes

In order to construct single-chain antibody genes (ScFv), a commonly used flexible linker consisting of 15 amino acids was added between the heavy chain variable region (VH) and light chain variable region (VL). The sequence of the linker was GGGGSGGGGSGGGGS (SEQ ID NO: 136) with encoding sequence of ggtggaggcggttctggcggag-gtgggagcggaggcggaggttca (SEQ ID NO: 137). The structure of the designed single-chain antibody was VH-Linker-VL.

Using the method described in the first section of this Example, many heavy chain and light chain variable region genes as shown in Table 3 below were obtained, including four different heavy chain variable region genes and three light chain variable region genes.

TABLE 3

Different heavy chain and light chain variable region genes.

| | heavy chain variable region | light chain variable region |
|---|---|---|
| Native antibody gene | VH | VL (VK + Vlmixed) |
| Synthesized antibody gene | VH1 | VK1 |
| | VH3 | VL3 |
| | VH5 | |

Based on the above design of single-chain antibodies and well-developed overlapping PCR technique, different heavy chains and light chains as shown in this Table could be conveniently combined. A total of 12 different single-chain antibody genes were constructed. The 12 single-chain antibody genes amplified by PCT reactions were purified and recovered by agarose gel electrophoresis, and stored at −20° C. for further use.

1.3 Construction of Arabinose Promoter-Based Phage Display Vector

Common phage display vectors are based on lac promotors (Plac). However, lac promotors impact the capability and diversity of the antibody library due to the properties thereof such as leaked expression. We engineered a common phage display vector pCANTAB5E (Amersham Biosciences/GE, Inc.) by using conventional molecular biology techniques as follows.

By dual enzyme digestion of AflIII and NotI, the Plac promoter and g3 signal peptide portion in the pCANTAB5E vector were replaced with a fragment comprising AraC gene, arabinose promoter (Para) and PelB leader, in which the AraC gene and Para were from the pBADhis vector from Invitrogen Inc., and the PelB leader sequence (SEQ ID NO: 6) was an artificial sequence. Then, by dual enzyme digestion of NcoI and NotI, a stuff sequence of about 750 bp (SEQ ID NO: 7) was cloned between NcoI and NotI, thereby constructing the final novel phage display vector pAD-SCFV-S (FIG. 1). The NcoI and NotI sites in this vector could facilitate cloning of a single-chain antibody (ScFv) gene.

1.4 Preparation of Human Single-Chain Antibody Library and Phage Display Antibody Library By conventional molecular biology techniques and dual enzyme digestion of NcoI and NotI, 12 ScFvs prepared in Section 1.2 were respectively cloned into the vector pAD-SCFV-S. The ligation products were electrotransfected into TG1 competent cells, in which about 20 rounds of electrotransfection were performed for each sub-library and a total of about 240 rounds of electrotransfection were carried out. The capability of each sub-library was calculated by dilution methods. 30-40 colonies were randomly selected from each sub-library for sequencing, so as to calculate the accuracy of each sub-library. The capabilities and accuracies of the 12 sub-libraries were shown in Table 4. The total capability of the 12 sub-libraries reached 1.0*10E9 with average accuracy of more than 75%.

TABLE 4

Capabilities and accuracies of the 12 sub-libraries

| Sub-library | Capability | Accuracy |
|---|---|---|
| ScFv -VH1-VK1 | 4.79*10E7 | 81% |
| ScFv -VH1-VL3 | 3.72*10E7 | 76% |
| ScFv -VH1-VL | 2.2*10E7 | 70% |
| ScFv -VH3-VK1 | 2.2*10E7 | 83% |
| ScFv -VH3-VL3 | 3.14*10E7 | 78% |
| ScFv -VH3-VL | 7.7*10E7 | 70% |
| ScFv -VH5-VK1 | 2.68*10E7 | 74% |
| ScFv -VH5-VL3 | 2.5*10E7 | 76% |
| ScFv -VH5-VL | 9.2*10E7 | 84% |
| ScFv -VH-VK1 | 5.9*10E7 | 75% |
| ScFv -VH-VL3 | 7.7*10E7 | 72% |
| ScFv -VH-VL | 27.2*10E7 | 85% |

The 12 sub-libraries were respectively seeded in 2YTAG liquid medium (A: ampicillin, 100 µg/ml; G: glucose, 2%), and incubated at 37° C. with oscillation at 220 rpm to reach logarithmic phase (OD600=0.8). Then, the cells were infected with M13 helper phages (M13KO7, NEB Inc.). After infection, the medium was changed to 2YTAKA liquid medium (A: ampicillin, 100 µg/ml; K: kanamycin, 70 µg/ml; A: arabinose, 0.001%), and the cells were incubated overnight at 28° C. with oscillation at 220 rpm for phage amplification. Then, the PEG/NaCl precipitation method was used to prepare purified phages (phage-ScFv), which was then subjected to titration. Then, the phage-ScFvs from the 12 sub-libraries as prepared were mixed proportionally in view of the capabilities, thereby preparing a phage display human antibody library. The final titer of phage library was 6*10E12 cfu/ml. The product was stored at −70° C. This phage display antibody library could be used for screening human antibodies specific to various antigens of interest.

Example 2: Preparation of Recombinant Protein Antigens

Preparation of anti-IL17 monoclonal antibodies required use of multiple different recombinant proteins, including human (*homo sapiens*) IL17 (huIL17, SEQ ID NO:8), mouse (*Mus musculus*) IL17 (moIL17, SEQ ID NO:9), *Macaca mulatta* IL17 (mmIL17, SEQ ID NO:10), *Macaca fascicularis* IL17 (mfIL17, SEQ ID NO:11), and human IL17R extracellular region (IL17R, SEQ ID NO:12). Since these proteins have glycosylation modifications, a mammalian cell expression system is advantageous for maintaining the structures and functions of the recombinant proteins. In addition, to facilitate purification, His-tag (SEQ ID NO: 13) or human antibody Fc fragment (SEQ ID NO: 14) was added to the C-terminal of these recombinant proteins.

Based on the amino acid sequences of various recombinant proteins of interest recorded in the Uniprot database, the genes (comprising His-tag or Fc encoding gene) of the above recombinant proteins were designed and synthesized. By conventional molecular biology techniques, the synthesized recombinant protein genes were cloned into proper eukaryotic expression vectors (e.g., pcDNA3.1 from Invitrogen Inc.). Then, liposomes (e.g., 293fectin from Invitrogen Inc.) or other transfection agents (e.g., PEI) are used to transfect the recombinant protein expression plasmids as prepared into HEK293 cells (e.g., HEK293F from Invitrogen Inc.). The cells were incubated in suspension under serum-free condition for 3-4 days. Then, supernatant of the culture was harvested by centrifugation.

For recombinant proteins fused with His-tags, the recombinant proteins in the supernatant were further purified using metal chelate affinity chromatography columns (e.g., His-Trap FF from GE Inc.). For recombinant proteins fused with Fc, Protein A/G affinity chromatography columns (e.g., Mabselect SURE from GE Inc.) was used for further purification. Then, desalination columns (e.g., Hitrap desaulting from GE Inc.) were used to change the storing buffer of the recombinant proteins to PBS (pH7.0) or other appropriate buffers. If necessary, the antibody samples could be subjected to filtration sterilization, and then split and stored at −20° C.

Example 3: Preparation of Anti-Human IL17 Monoclonal Antibodies Using Phage Display Antibody Library Technique

3.1 Enrichment of Anti-Human IL17Monoclonal Antibodies in Phage Antibody Library huIL17-his (hereafter referred to as "IL17-His") (5 µg/ml) was used as an antigen to coat an ELISA plate (150 µl/well, four wells in total). The plate was incubated overnight at 4° C. PBST-1% BSA was used to block the ELISA plate at 37° C. for 1 h. In the meantime, the phage display antibody library (phage-scFv) prepared in Example 1 was blocked with PBST-1% BSA at room temperature for 1 h with the input amount of phages being approximately 10¹². After blocking, the phage antibody library was added into the ELISA plate for antibody-to-antigen binding at 37° C. for 1 h. Unbound phages were removed by washing with PBST/PBS. Finally, 0.1M Glycine-HCl solution (pH2.2) was used to elute bound phages, and the eluted phages were neutralized with 1.5M Tris-HCl solution (pH8.8).

The neutralized phages were used to infect TG1 bacteria that had grown to logarithmic phase. The bacteria were incubated at 37° C. for 30 min, and oscillated at 150 rpm at 37° C. for 30 min 1% of the bacteria solution was plated for counting, and the rest solution was centrifuged at 4000 rpm for 5 min After removal of supernatant, the bacteria were plated onto 2YTAG solid medium (A: ampicillin, 100 μg/ml; G: glucose, 2%) in a dish, and incubated overnight at 33° C. for next screening procedure.

Bacteria on the dish were collected. A proper amount of collected bacteria were seeded into 2YTAG liquid medium (A: ampicillin, 100 μg/ml; G: glucose, 2%) and incubated with oscillation to reach logarithmic phase. The bacteria were infected with M13KO7. After infection, the medium was changed to 2YTAKA liquid medium (A: ampicillin, 100 μg/ml; K: kanamycin, 70 μg/ml; A: arabinose, 0.001%), and the bacteria were incubated overnight at 28° C. with oscillation at 220 rpm for phage amplification. PEG/NaCl precipitation method was used to purify phages for next screening procedure. A total of three rounds of phage library enrichment screening were carried out.

3.2 Identification of Anti-IL17 Single Colonies

After three rounds of screening, well-separated single colonies were picked and seeded into a 96-well plate containing 2YTAG medium, and incubated at 37° C. at 220 rpm to reach logarithmic phase. About 10¹⁰ helper phage M13KO7 was added to each well. The plate was incubated at 37° C. for 30 min, oscillated at 150 rpm at 37° C. for 30 min, and centrifuged at 2000 rpm at room temperature for 10 min After removal of supernatant, the bacteria were resuspended in 2YTAKA medium (A: ampicillin, 100 μg/ml; K: kanamycin, 70 μg/ml; A: arabinose, 0.001%), and incubated overnight at 28° C. with oscillation at 220 rpm.

IL17-Fc was coated with a carbonate buffer (pH9.6), and incubated overnight at 4° C. After washing three times with PBST, a PBST-4% milk solution was used for blocking at 37° C. for 1 h. The supernatant from overnight incubated monoclonal phage culture was proportionally diluted into PBST-4% milk, which was added at 100 μl/well to the blocked ELISA plate to bind at 37° C. for 1 h. The ELISA plate was washed with PBST. HRP-anti-M13 antibody was diluted at 1:5000, and added to the ELISA plate at 100 μl/well. After incubation at 37° C. for 1 h, an OPD developing solution was added to develop for 5-20 min. Then, 1M $H_2SO_4$ was added at 50 ml/well to terminate the development. Optical densities were determined using a microplate reader at the dual-wavelength of 492 nm/630 nm.

Following the above procedures, approximately 300 single colonies were obtained, among which four strains with single-chain antibodies (scFv) having different sequences and relatively high affinity to IL17 were identified, which were named as 11A, 9G, 3E and 6D.

3.3 Preliminary Functional Analysis of Anti-IL17 Monoclonal Antibodies

The four monoclonal strains (11A, 9G, 3E, 6D) were seeded into 2YTAG liquid medium, and incubated to reach logarithmic phase. The helper phage M13KO7, the amount of which is approximately 20-times of bacterium number, was added for infection. After infection, the medium was changed to 2YTAKA medium, and the cells were incubated overnight at 28° C. with oscillation at 220 rpm for phage amplification. PEG/NaCl precipitation method was used to purify phages.

IL17-his was coated with a carbonate solution (pH9.6), and incubated overnight at 4° C. After washing three times with PBST, a PBST-4% milk solution was used for blocking at 37° C. for 1 h. The four phages were diluted to a titer of 5*10E11 cfu/ml. The dilutions of the four phages were used to dilute IL17R-his. The starting concentration of IL17R-his was 20 μg/ml. A three-time gradient dilution was carried out with each sample containing seven rounds of dilutions. The dilutions were added to an ELISA plate at 100 μl/well, and incubated at 37° C. for 1 h. Then, a PBST solution was used to wish the ELISA plate. An HRP-anti-M13 secondary antibody was diluted at 1:5000, and added to the ELISA plate at 100 μl/well. After incubation at 37° C. for 1 h, an OPD developing solution was added to develop for 5-20 min. Then, 1M $H_2SO_4$ was added at 50 ml/well to terminate the development. Optical densities were determined using a microplate reader at the dual-wavelength of 492 nm/630 nm.

Figure 2:
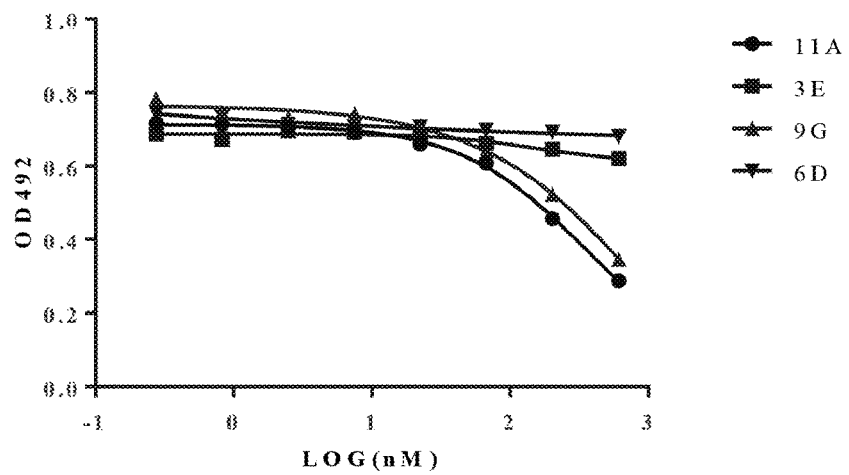
FIG. 2 shows competitive binding of a monoclonal phage and IL17R to IL17.

The results (see, FIG. 2) showed that single-chain antibodies 11A and 9G could compete with IL17R-his for binding to IL17-his, indicating that 11A (SEQ ID NO:15) and 9G (SEQ ID NO:16) have the same binding site for IL17 as IL17R. In contrast, single-chain antibodies 3E and 6D did not compete with IL17R-his, and are non-functional antibodies.

Example 4: Affinity Maturation of Anti-IL17 Monoclonal Antibodies Based on Light Chain Substitution Strategy

4.1 Construction of Dual Vector Display System Required for Affinity Maturation of Antibodies In order to facilitate introduction of mutations into the light chains and heavy chains of antibodies, three sets (six in total) of prokaryotic expression vectors that can co-exist in a single *E. coli* cell were constructed. Details were described as follows.

Figure 3:
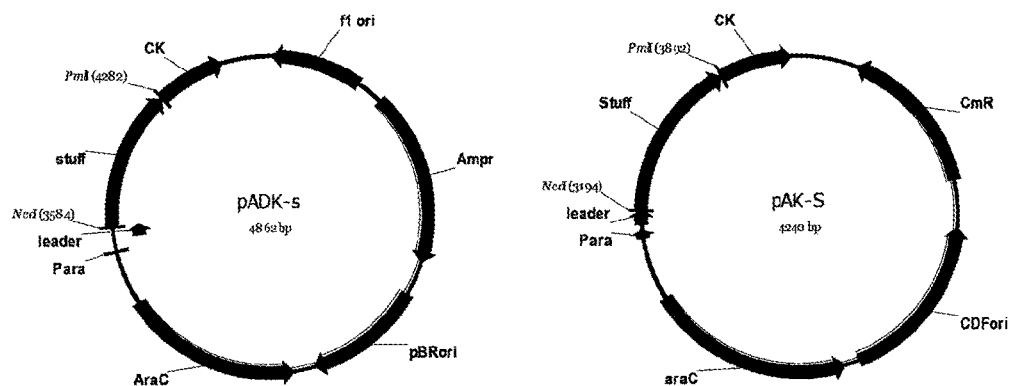
FIG. 3 shows structural diagrams of plasmids pADK-S and pAK-S (Para: arabinose promoter, leader: PelB signal peptide gene, NcoI: NcoI restriction site, Stuff: 750 bp stuff sequence, PmlI: PmlI restriction site, CK: kappa light chain constant region gene of human antibody; flori: replication origin of M13 phage, Ampr: ampicillin resistance gene, pBRori: replication origin of pBR322, AraC: AraC gene, CmR: chloromycetin resistance gene, CDFori: replication origin of CDF plasmid).

Using the plasmid pADSCFV-S in Example 1 as a mother plasmid and dual enzyme digestion of PmlI and XbaI, the kappa light chain constant region gene of the synthesized human antibody (SEQ ID NO:17) was cloned into the vector pADSCFV-S to replace the gIII gene in the initial vector, thereby constructing the vector pADK-S (see, FIG. 3). This vector could be used to clone and express the kappa light chain gene of human antibody.

Similarly, using the plasmid pADSCFV-S in Example 1 as a mother plasmid and dual enzyme digestion of PmlI and XbaI, the fusion gene of the heavy chain constant region CH1 of the synthesized human antibody and the C-terminal domain of the gIII protein (SEQ ID NO: 18) or the lambda light chain constant region of the human antibody (SEQ ID NO:19) was cloned into the vector pADSCFV-S to replace the gIII gene in the initial vector, thereby constructing the vectors pADG-S and pADL-S.

Chloramphenicol-resistant gene (CmR) was amplified from the pACYC184 plasmid (NEB Inc.) by PCR. The replication origin gene of the CDF plasmid (CDFori, SEQ ID NO: 20) was artificially synthesized. Then, by using conventional overlapping PCR method, a CmR-CDoriF fusion gene was constructed (XbaI and AflIII sites were added to two ends respectively). Then, by dual enzyme digestion of XbaI and AflIII, the CmR-CDFori fusion gene was cloned into the vectors pADK-S, pADG-S and pADL-S respectively to replace the flori-Ampr-pBRori segment, thereby constructing three new plasmids pAK-S (see, FIG. 3), pAG-S and pAL-S.

4.2 Construction of a Human Antibody Light Chain Library for Light Chain Substitution Procedure In order to facilitate light chain substitution procedure of antibodies, the plasmids pADK-S and pADL-S were used as mother plasmids to construct a high-quality human antibody light chain library. Details were described as follows.

By conventional PCR technique, VK1 genes were amplified by using the DNA from the four sub-libraries containing VK1 variable region genes prepared in Example 1 as templates and the primers shown in Table 5. Then, by dual enzyme digestion of NcoI and PmlI, the amplified VK1 genes were cloned into the vector pADK-S to replace the stuff sequence. The ligation products were electrotransfected into TG1 competent cells, thereby constructing a human VK1 light chain library. The capability of the library was calculated by dilution methods. 30 colonies were randomly selected for sequencing, so as to calculate the accuracy of each VK1 light chain library. The results were shown in Table 6.

Similarly, VL3 genes were amplified by using the DNA from the four sub-libraries containing VL3 variable region genes prepared in Example 1 as templates and the primers shown in Table 5. Then, by dual enzyme digestion of NcoI and PmlI, the amplified VL3 genes were cloned into the vector pADL-S to replace the stuff sequence. The ligation products were electrotransfected into TG1 competent cells, thereby constructing a human VL3 light chain library. The capability of the library was calculated by dilution methods. 30 colonies were randomly selected for sequencing, so as to calculate the accuracy of each VL3 light chain library. The results were shown in Table 6. The total capabilities of the two light chain libraries were 1.0*10E8 with accuracies over 90%.

Then, the two prepared light chain sub-libraries were respectively seeded in 2YTAG (A: ampicillin, 100 ug/ml; G: glucose, 2%) liquid medium, and incubated to reach logarithmic phase. Then, the cells were infected with M13 helper phages (M13KO7). After infection, the medium was changed to 2YTAKG (A: ampicillin, 100 μg/ml; K: kanamycin, 70 μg/ml; G: glucose, 2%) liquid medium, and the cells were incubated overnight at 28° C. at 220 rpm for phage amplification. Then, the PEG/NaCl precipitation method was used to prepare purified phages, which were then subjected to titration. Then, the phages from the two prepared sub-libraries were mixed proportionally in view of the capabilities, thereby preparing a phage library (phage-VK1+VL3) for assembling human antibody light chains. The final titer of phage library was 5.4*10E11 cfu/ml. The product was stored at −70° C. This phage library could be used in light chain substitution procedures of various antibodies.

TABLE 5

Primers for constructing VK1 and VL3 light chain libraries

| Use of primer | Primer | | SEQ ID NO: |
|---|---|---|---|
| Construction of VK1 light chain library | PVK1F1: | CCAGCCATGGCCGATATCCAGAT GACCCA | 126 |
| | PVK1R1: | CGTACGTTTGATCTCCACTTTGG TGC | 127 |
| Construction of VL3 light chain library | PVL3F1: | CCAGCCATGGCCAGCTACGAACT GACCCAGCC | 128 |
| | PVL3R1: | GGTCAGTTTGGTGCCACCGC | 129 |

TABLE 6

Capabilities and accuracies of VK1 and VL3 light chain libraries.

| Sub-library | Capability | Accuracy |
|---|---|---|
| pADK-VK1 | 7.2*10E7 | 95% |
| pADL-VL3 | 3.7*10E7 | 90% |

4.3 Light Chain Substitution Procedures of Anti-IL17 Antibodies

The light chains (11AVK, 9GVK) and heavy chains (11AVH, 9GVH) of the two single-chain antibodies 11A and 9G screened from the human antibody library were cloned into prokaryotic expression vectors pADK-s and pAG-s, respectively, thereby obtaining plasmids pADK-11AVK, pADK-9GVK, pAG-11AVH, pAG-9GVH expressing respective light chains and heavy chains. The heavy chain plasmids (pAG-11AVH, pAG-9GVH) were used to transform TG1 cells. Then, the cells were infected with phage packing the light chain library (phage-VK1+VL3), thereby obtaining the mutated light chain libraries of the two antibodies (11AVH-VK1+VL3 and 9GVH-VK1+VL3).

Then, the two mutated light chain libraries (11AVH-VK1+VL3 and 9GVH-VK1+VL3) were respectively seeded in 2YTACG liquid medium (A: ampicillin, 100 μg/ml; C: chloramphenicol, 34 μg/ml; G: glucose, 2%), and incubated to reach logarithmic phase. Then, the cells were infected with M13 helper phages (M13KO7). After infection, the medium was changed to 2YTACKA (A: ampicillin, 100 μg/ml; C: chloramphenicol, 34 μg/ml; K: kanamycin, 70 μg/ml; A: arabinose, 0.001%) liquid medium, and the cells were incubated overnight at 28° C. at 220 rpm for phage amplification. Then, the PEG/NaCl precipitation method was used to prepare purified phage library (phage-11AVH-VK1+VL3 and phage-9GVH-VK1+VL3), which was then subjected to titration. Then, the two phage libraries were mixed in equal proportion. The final titer of phage library was 1.9*10E13 cfu/ml. The product was stored at −70° C.

By conventional phage display methodology and technique, IL17-His was used in two rounds of enrichment of the phage-11AVH-VK1+VL3 and phage-9GVH-VK1+VL3 mixed library. Then, the phage ELISA method was used to identify the enriched single colonies (approximately 400 colonies). The colonies with high ELISA signal values were selected for sequencing. The colonies with correct sequence results were used to prepare purified phages. Meanwhile, the plasmids expressing the light chains and heavy chains of the two antibodies (11A and 9G) were co-transformed into TG1 cells. Purified phages were prepared as the positive control.

Figure 4:
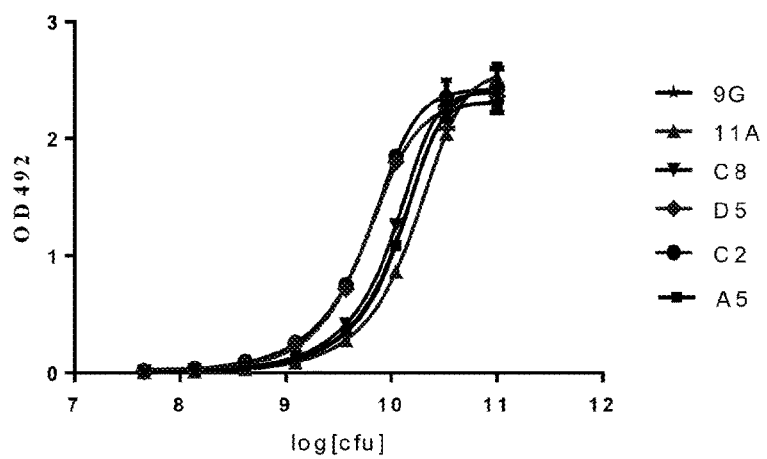
FIG. 4 shows measurement of relative affinity of phage antibodies by phage ELISA assays.

4.4 Comparison of Relative Affinities of Anti-IL17 Monoclonal Antibody Mutants by Purified Phage ELISA The titers of the multiple purified monoclonal phages were adjusted to 1*10E11/cfu. A three-time gradient dilution was carried out using PBST-4% milk solution. Coated IL17-Fc (2 μg/ml) and conventional phage ELISA method were used to analyze the IL17-binding capabilities of the phage antibodies in individual dilutions. The phage-ELISA results showed that, the several phage antibodies screened from the light chain substitution procedure carried out on 11A and 9G were all capable of binding to IL17. In addition, the relative affinities of C2 (SEQ ID NO: 21) and D5 (SEQ ID NO: 22) were substantially higher than those of other colonies (see, FIG. 4). It was noted that the heavy chains of C2 and D5 were 9GVH.

Example 5: Construction and Screening of 9G Heavy Chain Variable Region (9GVH) Mutant Library In order to further improve the affinity of the anti-IL17 monoclonal antibody, a 9G heavy chain variable region mutant library was constructed. The dual vector display system was used to screen the heavy chain mutant library.

9G heavy chain variable region gene (9GVH, SEQ ID NO: 23) was used as a template. By using conventional PCR technique and the degenerate primers shown in Table 7, various designed mutations were introduced into the CDRs of 9GVH. Then, overlapping PCR method was used in assembling procedure to obtain mutated genes of intact 9G heavy chain variable regions. By dual enzyme digestion of NcoI and PmlI, mutated 9GVH genes were cloned into the vector pADG-S. The ligation products were transformed into TG1 competent cells by electroporation, thereby constructing a 9GVH mutant library with library capability of approximately 4*10E6. 20 single colonies were randomly selected for sequencing. The results showed that the accuracy of the mutant library was 70% (14/20).

Then, the constructed 9GVH mutant library (TG1 bacteria) was seeded in 2YTAG liquid medium (A: ampicillin, 100 ug/ml; G: glucose, 2%), and incubated to reach logarithmic phase. Then, the cells were infected with M13 helper phages (M13KO7). After infection, the medium was changed to 2YTAKG (A: ampicillin, 100 μg/ml; K: kanamycin, 70 μg/ml; G: glucose, 2%) liquid medium, and the cells were incubated overnight at 28° C. at 220 rpm for phage amplification. Then, the PEG/NaCl precipitation method was used to prepare purified phages packing the 9GVH mutant library (phage-9GVH), which was then subjected to titration. The final titer of phage library was 1.4*10E13 cfu/ml. The product was stored at −70° C.

TABLE 7

Primers for introducing mutations into individual CDRs of 9G heavy chain (9GVH)

| CDRs | Primer | SEQ ID NO: |
|---|---|---|
| HCDR1 | P9GF1: CCAGCCATGGCCGAGGTG | 130 |
| | P9GR1: TCGGACCCAATTCATCCAGTAGTYGYYSAHGKW SAHTCCAGAGGCTGCACAGG | 131 |
| HCDR2 | P9GF2: TACTGGATGAATTGGGTCCG | 132 |
| | P9GR2: CACAGAGCCCACATAGTATTTCTCGKHGCCGYY TTGGKHSAHTGCGGCCACCCACTCCA | 133 |
| HCDR3 | P9GF3: GAGAAATACTATGTGGGCTCTGTG | 134 |
| | P9GR3: CGAAGTACCAGTAGTGTATGTAATAATCGCTAA TGAVATCGTAATAGTCTCTCACACAG | 135 |

By conventional PCR technique, the two light chain genes C2 and D5 screened in Example 4 were cloned into the vector pAK-S which was then transformed into TG1 bacteria, thereby obtaining the two strains pAK-C2/TG1 and pAK-D5/TG1. Then, the phage library (phage-9GVH) was used to infect pAK-C2/TG1 and pAK-D5/TG1 at logarithmic phase, thereby obtaining two 9GVH mutant libraries (light chains were C2 and D5, respectively).

Then, in accordance with conventional phage display protocols, M13KO7 was used for infection. The two Fab libraries containing 9GVH mutants were respectively displayed on the surfaces of phages, thereby preparing two Fab phage display libraries (phage-C2-9GVH and phage-D5-9GVH). The two phage display libraries were mixed in equal proportion. IL17-his was used for two rounds of screening phage-C2-9GVH and phage-D5-9GVH mixed library. Approximately 300 colonies were selected for monoclonal phage ELISA identification. Finally, three 9GVH mutant strains were selected for subsequent test, which were named as 9GA3 (SEQ ID NO: 24), 9GC2 (SEQ ID NO: 25) and 9GC5 (SEQ ID NO: 26). In addition, these three 9GVH mutants all had the best matching light chain C2 (SEQ ID NO: 21).

Example 6: Expression and Purification of Monoclonal Antibodies

Since antibodies are large proteins containing complicated post-translation modifications, the expression of a recombinant intact antibody usually takes advantage of a mammalian cell expression system. In addition, by using the protein A/G affinity chromatography method, antibodies can be easily purified to reach purity above 95%. This example briefly describes methods and technique for preparing conventional recombinant antibodies.

By using conventional molecular biology technique, the heavy chain and light chain genes of an antibody of interest were cloned into an appropriate eukaryotic expression vector (e.g., pcDNA3.1 from Invitrogen Inc.). The antibody heavy chain constant region could be of IgG1 subtype (SEQ ID NO: 29) or IgG4 subtype (SEQ ID NO: 30), and the light chain constant region could be of kappa subtype (SEQ ID NO: 31) or lambda subtype (SEQ ID NO: 32).

Then, liposomes (e.g., 293fectin from Invitrogen Inc.) or other transfection agents (e.g., PEI) were used to co-transfect plasmids expressing the heavy chain and the light chain as prepared into HEK293 cells (e.g., HEK293F from Invitrogen Inc.) or CHO cells (e.g., CHO-S from Invitrogen Inc.). The cells were incubated in suspension under serum-free condition for 3-4 days. Then, supernatant of the culture was harvested by centrifugation. Protein A/G affinity chromatography column (e.g., Mabselect SURE from GE Inc.) was used to further purify the recombinant antibody in the supernatant. Then, desalination columns (e.g., Hitrap desaulting from GE Inc.) were used to change the storing buffer of the antibody to PBS (pH7.0) or other appropriate buffers (e.g., 0.1NaCl, 0.01M sodium citrate, pH 6.0). If necessary, the antibody samples could be subjected to filtration sterilization, and then split and stored at −20° C.

Example 7: Binding Assay of Anti-IL17 Monoclonal Antibody and Human IL17

The IL17-His-binding capabilities of four anti-IL17 monoclonal antibodies 9GA3, 9GC2, 9GC5 and a control antibody Secukinumab (VH: SEQ ID NO:27, VK: SEQ ID NO:28) were assessed using ELISA assays.

Figure 5:
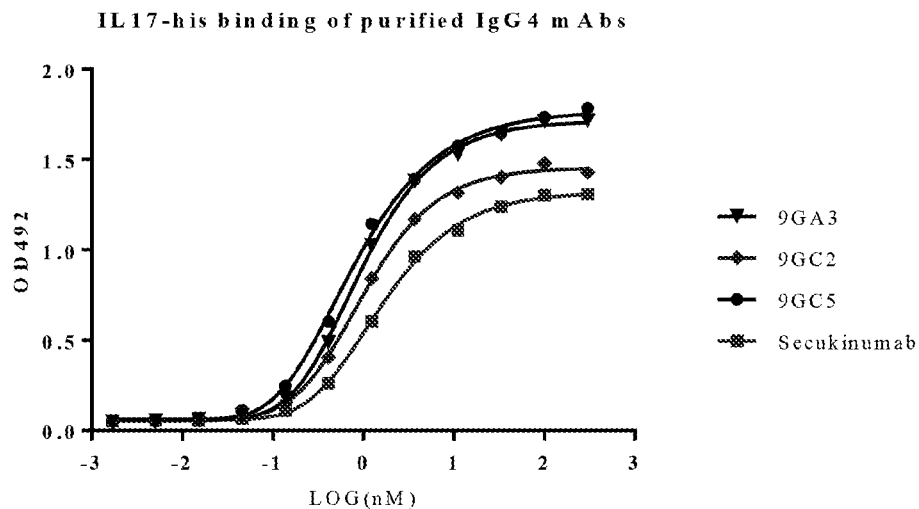
FIG. 5 shows binding capability of anti-IL17 antibodies to human IL17 as measured by ELISA assays.

IL17-his was used to coat plates overnight at 4° C. (0.5 µg/ml, 100 µl/well). Each monoclonal antibody had a starting concentration of 300 nM, and was subjected to a three-time gradient dilution. Eleven gradient dilutions were set for each monoclonal antibody sample. HRP-goat-anti-human IgG was used to determine the IL17-binding capabilities of the monoclonal antibodies at each dilution (see, FIG. 5).

Figure 6:
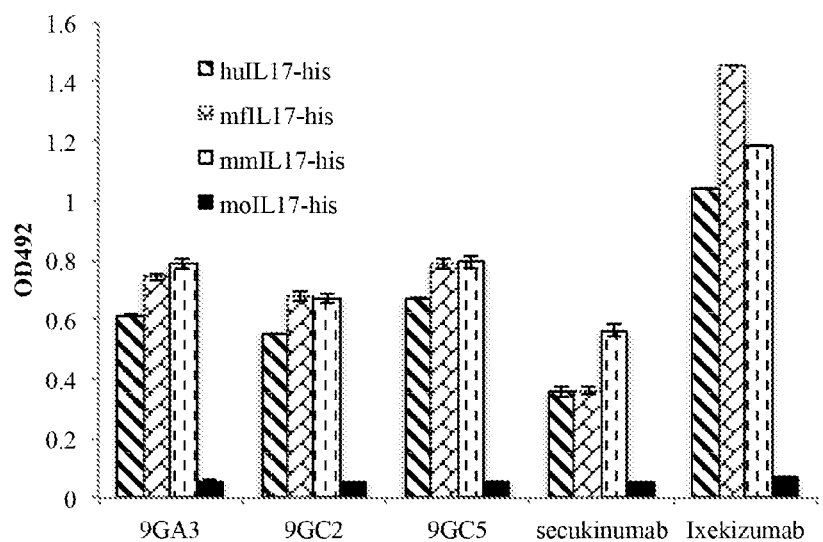
FIG. 6 shows binding capability of anti-IL17 monoclonal antibodies to IL17 proteins from different species as measured by ELISA assays.

Example 8: Binding Between Anti-IL17 Monoclonal Antibodies and IL17 from Different Species Four kinds of prepared IL17 (huIL17, mIL17, mmIL17, and mfIL17) were used to coat 96-well ELISA plates overnight at 4° C. (1 µg/ml, 100 µl/well). A blocking solution (2% milk powder-PBST) was added, and the plates were incubated at 37° C. for 1 h. Then, various anti-IL17 monoclonal antibodies, including 9GA3, 9GC2, 9GC5, secukinumab and Ixekizumab (VH: SEQ ID NO:33, VK: SEQ ID NO:34), were added and allowed to bind at 37° C. for 1 h. Then, the plates were washed four times with PBST. Then, HRP-anti-human IgG (a secondary antibody) was added, and allowed to incubate at 37° C. for 1 h. Then, the plates were washed four times with PBST. An OPD developing solution was added to develop for 5-10 min. Then, 1M $H_2SO_4$ was added to terminate the development. The microreader from Molecular Device (Spectra Max190) was used to determine optical densities at 492 nm. As shown in the results in FIG. 6, the anti-IL17 monoclonal antibodies of the invention and the control antibodies could recognize human, *Macaca mulatta* and *Macaca fascicularis* IL17, but did not bind to mouse IL17.

Example 9: Competitive IL17-Binding of Anti-Human IL17 Monoclonal Antibodies with IL17 Receptor (IL17R)

A functional anti-IL17 monoclonal antibody should be able to block the binding of IL17R to IL17 at protein level. In this Example, the abilities of four anti-IL17 monoclonal antibodies (9GA3, 9GC2, 9GC5, and secukinumab) to inhibit the binding of IL17R to IL17 were assessed.

Figure 7:
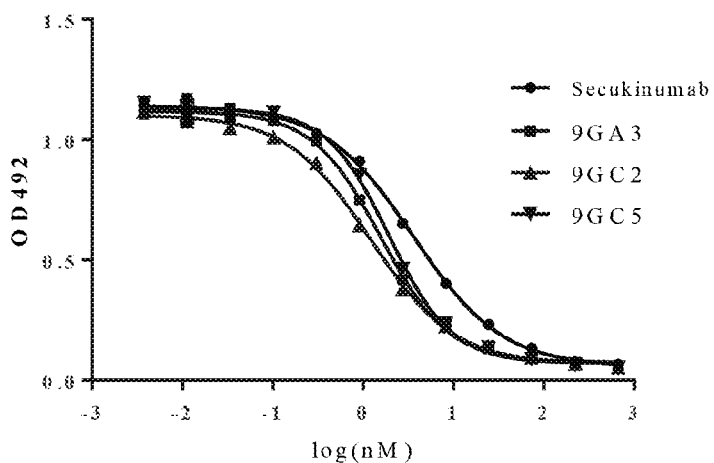
FIG. 7 shows competitive binding of anti-huIL17 monoclonal antibodies and IL17R to IL17.

IL17-Fc was used to coat plates overnight at 4° C. (0.5 µg/well, 100 µl/well). Each monoclonal antibody (starting concentration of 200 µg/ml) was subjected to a three-time gradient dilution with IL17R-his (2 µg/ml). Ten gradient dilutions were set for each monoclonal antibody. HRP-mouse-anti-his monoclonal antibody was used to determine the binding signal between IL17R-his and IL17-Fc. Then, GraphPad Prism 6 was used for data analysis and plotting (see, FIG. 7).

HDFa cells (adult dermal fibroblasts) were purchased from Sciencell Inc. (Cat#:2320). The cells were cultured and passaged according to the instructions provided by Sciencell Inc.

Figure 8:
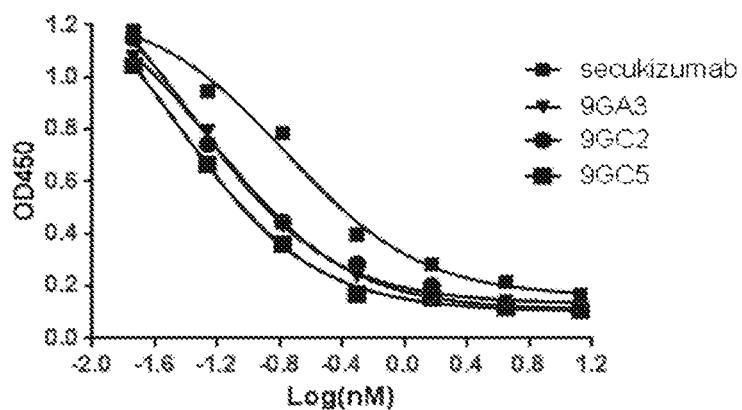
FIG. 8 shows comparison analysis of inhibition of IL17-induced IL6 production in HDFa cells by anti-IL17 monoclonal antibodies.

When the activities of the anti-IL17 monoclonal antibodies were assessed using HDFa cells, the HDFa cells were seeded in 96-well plates with cell density of 1*10E4 cells/well. 1% FBS was added to FM medium, and the other components were the same as complete FM medium. The cells were cultured overnight at 37° C. On the second day, the medium was changed to the medium (FM+1% FBS) containing 2 nM IL17-His and anti-IL17 monoclonal antibodies (9GA3, 9GC2, 9GC5, and secukinumab) at various concentrations (0.01-10 nM), and the cells were cultured for 24 h. Then, the supernatant of the culture was collected. IL6 quantification kit (Cat#:EHoo4-96) from Excell Biology Inc. was used to determine the amount of IL6 in the supernatant from each culture. Then, GraphPad Prism 6 was used for data analysis and plotting (see, FIG. 8). The $IC_{50}$ of each anti-IL17 monoclonal antibody in inhibiting the release of IL6 was shown in Table 8.

TABLE 8

$IC_{50}$ of four anti-IL17 monoclonal antibodies in inhibiting IL17-induced the release of IL6 by HDFa cells

| mAbs | 9GA3 | 9GC2 | 9GC5 | secukinumab |
|---|---|---|---|---|
| $IC_{50}$ (nM) | 0.12 | 0.22 | 0.07 | 0.48 |

Figure 9:
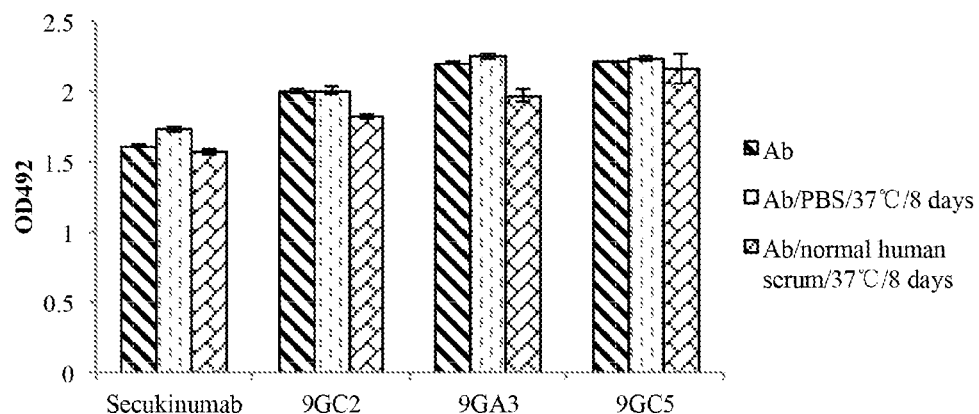
FIG. 9 shows stability analysis of various anti-IL17 monoclonal antibodies in human sera.

Example 10: Assessment of Stabilities of Anti-IL17 Monoclonal Antibodies in Human Serum In order to preliminarily assess the specificities and serum stabilities of various anti-IL17 monoclonal antibodies, assessment of stabilities of anti-IL17 monoclonal antibodies in human serum was carried out. This study involved four anti-IL17 monoclonal antibodies, i.e., 9GA3, 9GC2, 9GC5 and secukinumab. Purified monoclonal antibody samples were formulated in 0.01M sodium citrate, 0.1M NaCl, pH6.0. Monoclonal antibody samples, which had been subjected to filtration sterilization, were diluted in 200 µl sterile serum mixture from healthy subjects or PBS to a final concentration of 30 µg/ml. After sufficient mixing, the samples were placed in a water bath at 37° C. for eight days (192 h). After eight days, the human IL17-binding capabilities of serum samples (A), PBS samples (B) or frozen monoclonal antibody samples (C) were assessed by ELISA assays (see, FIG. 9). The alteration in IL17-binding capabilities of each monoclonal antibody sample was compared (A/C). As shown in Table 9 below, four anti-IL17 monoclonal antibodies had good serum stabilities.

TABLE 9

Alteration in IL17-binding capabilities of monoclonal antibody samples under different treatment conditions

| | monoclonal antibodies | | | |
|---|---|---|---|---|
| | 9GA3 | 9GC2 | 9GC5 | Secukinumab |
| A/C | 87% | 91% | 97% | 91% |

Example 11: In Vivo pK Assessment in Mice

In order to determine the in vivo metabolic properties of anti-IL17 monoclonal antibodies in mice, various anti-IL17 monoclonal antibodies were administered in a single dose via tail veins of mice to assess pK. This study involved four anti-IL17 monoclonal antibodies (IgG4 subtype), which were 9GA3, 9GC2, 9GC5 and Ixekizumab. Monoclonal antibody samples were formulated in PBS buffering system (pH7.0) at a concentration of 0.5 mg/ml. The administration dose was 5 mg/kg. Single-dose was administered via tail veins. Each group included eight BALB/c mice with hale male and half female. Serum samples were collected at 4, 24, 48, 96, 168, 240, and 336 h after administration (orbital blood sampling), and stored at −70° C. After all sampling, the concentrations of the monoclonal antibodies were determined.

Figure 10:
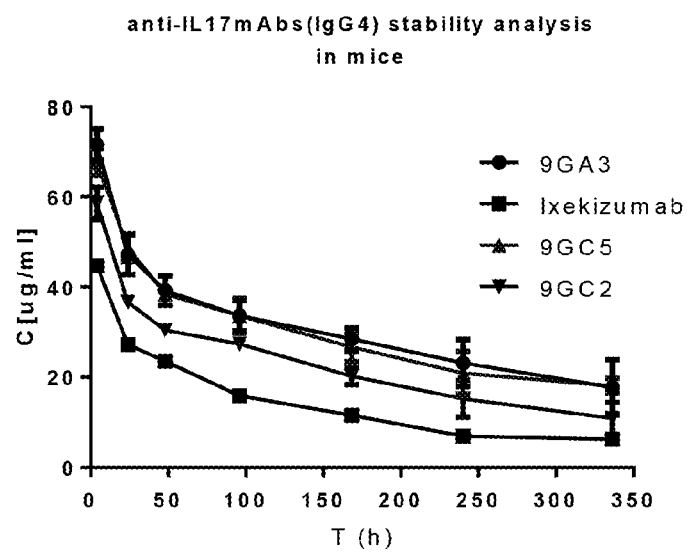
FIG. 10 shows concentration alteration trend of four anti-IL17 monoclonal antibodies in mice.

Quantification of blood concentrations was carried out by quantitative ELISA assay based on coated IL17. Four purified anti-IL17 monoclonal antibody samples (9GA3, 9GC2, 9GC5 and Ixekizumab) were used as standards in quantification, and standard curves were respectively established for use in quantification of blood concentrations of the monoclonal antibodies. The change trends of in vivo concentrations of the four monoclonal antibodies in mice are shown in FIG. 10.

According to the first-order reaction model, natural logarithms (InC) of antibody concentrations were plotted with respect to time (t), thereby calculating the slope constant k. Then, According to the formula t1/2=0.693/k, the in vivo half-lives (t1/2) of the four anti-IL17 monoclonal antibodies in mice were calculated. The results were shown in Table 10.

TABLE 10

In vivo half-lives (t½) of four anti-IL17 monoclonal antibodies in mice

| | monoclonal antibodies | | | |
|---|---|---|---|---|
| | 9GA3 | 9GC2 | 9GC5 | Ixekizumab |
| t½ (h) | 8.5 | 6.7 | 7.4 | 4.0 |

What is claimed is:

1. A monoclonal antibody that specifically binds to human IL-17A, comprising a heavy chain variable region comprising HCDR1, HCDR2 and HCDR3 and a light chain variable region comprising LCDR1, LCDR2 and LCDR3;
wherein HCDR1 has the sequence $GX_1X_2X_3X_4X_5Y$, HCDR2 has the sequence $NQDGX_6E$ (SEQ ID NO: 35), and HCDR3 has the sequence $DYYDX_7ISDYYIHYWYFDL$ (SEQ ID NO: 36), wherein the sequence $X_1X_2X_3X_4X_5$ is FTIDN (SEQ ID NO: 37), MSMSD (SEQ ID NO: 38) or ITMDD (SEQ ID NO: 39), $X_6$ is N or D, $X_7$ is V or L;
wherein LCDR1 has the sequence RASQNVHNRLT (SEQ ID NO: 40), LCDR2 has the sequence GASNLES (SEQ ID NO: 41), and LCDR3 has the sequence QQYNGSPTT (SEQ ID NO: 42); and
wherein HCDR1, HCDR2, HCDR3, LCDR1, LCDR2 and LCDR3 are defined according to Chothia.

2. The monoclonal antibody according to claim 1, wherein the heavy chain variable region of the antibody has the amino acid sequence as set forth in SEQ ID NO: 24, 25 or 26.

3. The monoclonal antibody according to claim 1, wherein the light chain variable region of the antibody has the amino acid sequence as set forth in SEQ ID NO: 21.

4. The monoclonal antibody according to claim 1, wherein
the heavy chain variable region of the antibody has the sequence as set forth in SEQ ID NO: 24, and the light chain variable region has the sequence as set forth in SEQ ID NO:21; or
the heavy chain variable region has the sequence as set forth in SEQ ID NO: 25, and the light chain variable region has the sequence as set forth in SEQ ID NO:21; or
the heavy chain variable region has the sequence as set forth in SEQ ID NO: 26, and the light chain variable region has the sequence as set forth in SEQ ID NO:21.

5. The monoclonal antibody according to claim 1, wherein the antibody is an intact antibody, a substantively intact antibody, a Fab fragment, a F(ab')2 fragment or a single chain Fv fragment.

6. The monoclonal antibody according to claim 5, wherein the antibody is a fully human antibody.

7. The monoclonal antibody according to claim 1, wherein the antibody further comprises a heavy chain constant region selected from the group consisting of IgG1 and IgG4 subtypes, and/or a light chain constant region selected from the group consisting of kappa and lambda subtypes.

8. The monoclonal antibody according to claim 1, wherein the monoclonal antibody is capable of inhibiting the activity of 2 nM human IL-17A by 50% at a concentration less than 1 nM, wherein the activity inhibition is measured by determining human IL-17A-induced IL-6 production in human dermal fibroblasts (HDFa).

9. The monoclonal antibody according to claim 1, wherein
HCDR1 has the sequence GFTIDNY (positions 26-32 of SEQ ID NO: 25), HCDR2 has the sequence NQDGNE (positions 52-57 of SEQ ID NO: 25), HCDR3 has the sequence DYYDVISDYYIHYWYFDL (positions 99-116 of SEQ ID NO: 25), or
HCDR1 has the sequence GMSMSDY (positions 26-32 of SEQ ID NO: 26), HCDR2 has the sequence NQDGDE (positions 52-57 of SEQ ID NO: 26), HCDR3 has the sequence DYYDLISDYYIHYWYFDL (positions 99-116 of SEQ ID NO: 26), or
HCDR1 has the sequence GITMDDY (positions 26-32 of SEQ ID NO: 24), HCDR2 has the sequence NQDGNE (positions 52-57 of SEQ ID NO: 24), HCDR3 has the sequence DYYDLISDYYIHYWYFDL (positions 99-116 of SEQ ID NO: 24).

10. A pharmaceutical composition, comprising a monoclonal antibody that specifically binds to human IL-17A, comprising a heavy chain variable region comprising HCDR1, HCDR2 and HCDR3 and a light chain variable region comprising LCDR1, LCDR2 and LCDR3;
wherein HCDR1 has the sequence $GX_1X_2X_3X_4X_5Y$, HCDR2 has the sequence $NQDGX_6E$ (SEQ ID NO: 35), and HCDR3 has the sequence $DYYDX_7ISDYYIHYWYFDL$ (SEQ ID NO: 36), wherein the sequence $X_1X_2X_3X_4X_5$ is FTIDN (SEQ ID NO: 37), MSMSD (SEQ ID NO: 38) or ITMDD (SEQ ID NO: 39), $X_6$ is N or D, $X_7$ is V or L;
wherein LCDR1 has the sequence RASQNVHNRLT (SEQ ID NO: 40), LCDR2 has the sequence GASNLES (SEQ ID NO: 41), and LCDR3 has the sequence QQYNGSPTT (SEQ ID NO: 42); and
wherein HCDR1, HCDR2, HCDR3, LCDR1, LCDR2 and LCDR3 are defined according to Chothia.

11. The pharmaceutical composition according to claim 10, wherein the heavy chain variable region of the antibody has the amino acid sequence as set forth in SEQ ID NO: 24, SEQ ID NO: 25 or SEQ ID NO: 26.

12. The pharmaceutical composition according to claim 10, wherein the light chain variable region of the antibody has the amino acid sequence as set forth in SEQ ID NO: 21.

13. The pharmaceutical composition according to claim 10, wherein
HCDR1 has the sequence GFTIDNY (positions 26-32 of SEQ ID NO: 25), HCDR2 has the sequence NQDGNE (positions 52-57 of SEQ ID NO: 25), HCDR3 has the sequence DYYDVISDYYIHYWYFDL (positions 99-116 of SEQ ID NO: 25), or
HCDR1 has the sequence GMSMSDY (positions 26-32 of SEQ ID NO: 26), HCDR2 has the sequence NQDGDE (positions 52-57 of SEQ ID NO: 26), HCDR3 has the sequence DYYDLISDYYIHYWYFDL (positions 99-116 of SEQ ID NO: 26), or HCDR1 has the sequence GITMDDY (positions 26-32 of SEQ ID NO: 24), HCDR2 has the sequence NQDGNE (positions 52-57 of SEQ ID NO: 24), HCDR3 has the sequence DYYDLISDYYIHYWYFDL (positions 99-116 of SEQ ID NO: 24).

14. A method of treating a human IL-17A-mediated disease comprising administering a monoclonal antibody that specifically binds to human IL-17A, comprising a heavy chain variable region comprising HCDR1, HCDR2 and HCDR3 and a light chain variable region comprising LCDR1, LCDR2 and LCDR3;

wherein HCDR1 has the sequence $GX_1X_2X_3X_4X_5Y$, HCDR2 has the sequence $NQDGX_6E$ (SEQ ID NO: 35), and HCDR3 has the sequence $DYYDX_7ISDYYIHYWYFDL$ (SEQ ID NO: 36), wherein the sequence $X_1X_2X_3X_4X_5$ is FTIDN (SEQ ID NO: 37), MSMSD (SEQ ID NO: 38) or ITMDD (SEQ ID NO: 39), $X_6$ is N or D, $X_7$ is V or L;

wherein LCDR1 has the sequence RASQNVHNRLT (SEQ ID NO: 40), LCDR2 has the sequence GASNLES (SEQ ID NO: 41), and LCDR3 has the sequence QQYNGSPTT (SEQ ID NO: 42); and wherein HCDR1, HCDR2, HCDR3, LCDR1, LCDR2 and LCDR3 are defined according to Chothia, wherein the disease is psoriasis, rheumatoid arthritis or ankylosing spondylitis.

15. The method according to claim 14, wherein the heavy chain variable region of the antibody has the amino acid sequence as set forth in SEQ ID NO: 24, 25 or 26.

16. The method according to claim 14, wherein the light chain variable region of the antibody has the amino acid sequence as set forth in SEQ ID NO: 21.

17. The method according to claim 14, wherein

HCDR1 has the sequence GFTIDNY (positions 26-32 of SEQ ID NO: 25), HCDR2 has the sequence NQDGNE (positions 52-57 of SEQ ID NO: 25), HCDR3 has the sequence DYYDVISDYYIHYWYFDL (positions 99-116 of SEQ ID NO: 25), or HCDR1 has the sequence GMSMSDY (positions 26-32 of SEQ ID NO: 26), HCDR2 has the sequence NQDGDE (positions 52-57 of SEQ ID NO: 26), HCDR3 has the sequence DYYDLISDYYIHYWYFDL (positions 99-116 of SEQ ID NO: 26), or HCDR1 has the sequence GITMDDY (positions 26-32 of SEQ ID NO: 24), HCDR2 has the sequence NQDGNE (positions 52-57 of SEQ ID NO: 24), HCDR3 has the sequence DYYDLISDYYIHYWYFDL (positions 99-116 of SEQ ID NO: 24).

* * * * *